(12) United States Patent
McNair

(10) Patent No.: US 11,232,860 B1
(45) Date of Patent: Jan. 25, 2022

(54) DISCOVERING CONTEXT-SPECIFIC SERIAL HEALTH TRAJECTORIES

(71) Applicant: Cerner Innovation, Inc., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 993 days.

(21) Appl. No.: 14/982,982

(22) Filed: Dec. 29, 2015

Related U.S. Application Data

(62) Division of application No. 14/175,750, filed on Feb. 7, 2014.
(Continued)

(51) Int. Cl.
*G16H 40/20* (2018.01)
*G16H 50/30* (2018.01)

(52) U.S. Cl.
CPC ............. *G16H 40/20* (2018.01); *G16H 50/30* (2018.01)

(58) Field of Classification Search
None
See application file for complete search history.

(56) References Cited

U.S. PATENT DOCUMENTS

| 4,839,853 A | 6/1989 | Deerwester et al. |
| 5,243,565 A | 9/1993 | Yamamoto |

(Continued)

FOREIGN PATENT DOCUMENTS

| EP | 1043666 A2 | 10/2000 |
| EP | 2365456 A2 | 9/2011 |

(Continued)

OTHER PUBLICATIONS

R.I John, P.R Innocent, M.R Barnes, Neuro-fuzzy clustering of radiographic tibia image data using type 2 fuzzy sets,Information Sciences, vol. 125, Issues 1-4, 2000, pp. 65-82, ISSN 0020-0255, https://www.sciencedirect.com/science/article/pii/S0020025500000098 (Year: 2000).*

(Continued)

*Primary Examiner* — Lena Najarian
(74) *Attorney, Agent, or Firm* — Shook Hardy & Bacon LLP

(57) ABSTRACT

Systems and methods are provided for injury characterization including detecting matches of an individual subject's record (such as an athlete's record) with collections of other subjects records, based on serial, longitudinal patterns, for facilitating athlete health and training, preventive and rehabilitation medicine, and risk management in athletics. In an embodiment, time series are formed from information pertaining to successive longitudinal episodes of injury and the circumstances in which the injuries were incurred; calculating time-series K-nearest-neighbor clusters and distances for each such combination; determining the cluster to which a given candidate player injury record is nearest or belongs, and prescribing an injury-risk reduction intervention specific to the plurality of hazards that are characteristic of trajectories that are members of that cluster and that are deemed to be relevant to reducing or mitigating those hazards and thereby are efficacious in preventing subsequent injuries that are prevalent in that trajectory cluster.

20 Claims, 17 Drawing Sheets

Related U.S. Application Data

(60) Provisional application No. 61/762,178, filed on Feb. 7, 2013.

(56) References Cited

U.S. PATENT DOCUMENTS

| | | |
|---|---|---|
| 5,301,109 A | 4/1994 | Landauer et al. |
| 5,664,109 A | 9/1997 | Johnson et al. |
| 5,809,494 A | 9/1998 | Nguyen |
| 5,835,900 A | 11/1998 | Fagg et al. |
| 6,039,688 A | 3/2000 | Douglas et al. |
| 6,122,628 A | 9/2000 | Castelli et al. |
| 6,246,964 B1 | 6/2001 | Blaunstein |
| 6,246,975 B1 | 6/2001 | Rivonelli et al. |
| 6,247,004 B1 | 6/2001 | Moukheibir |
| 6,397,224 B1 | 5/2002 | Zubeldia et al. |
| 6,618,715 B1 | 9/2003 | Johnson et al. |
| 6,654,740 B2 | 11/2003 | Tokuda et al. |
| 6,665,669 B2 | 12/2003 | Han et al. |
| 6,915,254 B1 | 7/2005 | Heinze et al. |
| 6,996,575 B2 | 2/2006 | Cox et al. |
| 7,039,634 B2 | 5/2006 | Xu et al. |
| 7,120,626 B2 | 10/2006 | Li et al. |
| 7,249,117 B2 | 7/2007 | Estes |
| 7,386,522 B1 | 6/2008 | Bigus et al. |
| 7,440,947 B2 | 10/2008 | Adcock et al. |
| 7,447,643 B1 | 11/2008 | Olson et al. |
| 7,496,561 B2 | 2/2009 | Caudill et al. |
| 7,529,765 B2 | 5/2009 | Brants et al. |
| 7,555,425 B2 | 6/2009 | Oon |
| 7,558,778 B2 | 7/2009 | Darus et al. |
| 7,617,078 B2 | 11/2009 | Rao et al. |
| 7,640,171 B2 | 12/2009 | Gendron et al. |
| 7,657,540 B1 | 2/2010 | Bayliss |
| 7,668,820 B2 | 2/2010 | Zuleba |
| 7,720,846 B1 | 5/2010 | Bayliss |
| 7,831,423 B2 | 11/2010 | Schubert |
| 7,844,449 B2 | 11/2010 | Lin et al. |
| 7,844,566 B2 | 11/2010 | Wnek |
| 7,853,456 B2 | 12/2010 | Soto et al. |
| 7,865,373 B2 | 1/2011 | Punzak et al. |
| 7,899,764 B2 | 3/2011 | Martin et al. |
| 7,899,796 B1 | 3/2011 | Borthwick et al. |
| 7,900,052 B2 | 3/2011 | Jonas |
| 7,912,842 B1 | 3/2011 | Bayliss |
| 7,933,909 B2 | 4/2011 | Trepetin |
| 7,953,685 B2 | 5/2011 | Liu et al. |
| 8,015,136 B1 | 9/2011 | Baker et al. |
| 8,078,554 B2 | 12/2011 | Fung et al. |
| 8,126,736 B2 | 2/2012 | Anderson et al. |
| 8,160,895 B2 | 4/2012 | Schmitt et al. |
| 8,165,893 B1 | 4/2012 | Goldberg et al. |
| 8,200,505 B2 | 6/2012 | Walker et al. |
| 8,515,777 B1 | 8/2013 | Rajasenan |
| 8,539,424 B2 | 9/2013 | Tetelbaum |
| 8,589,424 B1 | 11/2013 | Patel et al. |
| 8,666,785 B2 | 3/2014 | Baluta et al. |
| 8,838,628 B2 | 9/2014 | Leighton et al. |
| 8,856,156 B1 | 10/2014 | McNair et al. |
| 9,375,142 B2 | 6/2016 | Schultz et al. |
| 9,542,532 B1 | 1/2017 | McNair et al. |
| 9,542,647 B1 | 1/2017 | Mirhaji |
| 9,734,146 B1 | 8/2017 | McNair et al. |
| 10,198,499 B1 | 2/2019 | McNair et al. |
| 10,249,385 B1 | 4/2019 | McNair et al. |
| 10,268,687 B1 | 4/2019 | McNair et al. |
| 10,431,336 B1 | 10/2019 | Murrish et al. |
| 10,446,273 B1 | 10/2019 | McNair et al. |
| 10,483,003 B1 | 11/2019 | McNair et al. |
| 10,580,524 B1 | 3/2020 | McNair et al. |
| 10,628,553 B1 | 4/2020 | Murrish et al. |
| 10,769,241 B1 | 9/2020 | McNair |
| 10,957,449 B1 | 3/2021 | Mcnair et al. |
| 2002/0032583 A1 | 3/2002 | Joao |
| 2002/0035486 A1 | 3/2002 | Huyn et al. |
| 2002/0038227 A1 | 3/2002 | Fey et al. |
| 2002/0038308 A1 | 3/2002 | Cappi |
| 2002/0042793 A1 | 4/2002 | Choi |
| 2002/0073138 A1 | 6/2002 | Gilbert et al. |
| 2002/0128860 A1 | 9/2002 | Leveque et al. |
| 2003/0023571 A1 | 1/2003 | Barnhill |
| 2003/0038308 A1 | 2/2003 | Kim |
| 2003/0163057 A1 | 8/2003 | Flick et al. |
| 2003/0212580 A1 | 11/2003 | Shen |
| 2004/0199332 A1 | 10/2004 | Iliff |
| 2004/0230105 A1 | 11/2004 | Geva et al. |
| 2004/0260666 A1 | 12/2004 | Pestotnik et al. |
| 2005/0027562 A1 | 2/2005 | Brown |
| 2005/0049497 A1 | 3/2005 | Krishnan et al. |
| 2005/0119534 A1 | 6/2005 | Trost et al. |
| 2005/0144042 A1 | 6/2005 | Joffe et al. |
| 2005/0272984 A1 | 12/2005 | Huiku |
| 2005/0288910 A1 | 12/2005 | Schlessinger et al. |
| 2006/0020465 A1 | 1/2006 | Cousineau et al. |
| 2006/0064447 A1 | 3/2006 | Malkov |
| 2006/0074824 A1 | 4/2006 | Li |
| 2006/0129427 A1 | 6/2006 | Wennberg |
| 2006/0161457 A1 | 7/2006 | Rapaport et al. |
| 2006/0173663 A1 | 8/2006 | Langheier et al. |
| 2006/0205564 A1 | 9/2006 | Peterson |
| 2006/0206027 A1 | 9/2006 | Malone |
| 2006/0206359 A1 | 9/2006 | Stang |
| 2006/0218010 A1 | 9/2006 | Michon et al. |
| 2006/0271556 A1 | 11/2006 | Mukherjee et al. |
| 2007/0005621 A1 | 1/2007 | Lesh et al. |
| 2007/0026365 A1 | 2/2007 | Friedrich et al. |
| 2007/0031873 A1 | 2/2007 | Wang et al. |
| 2007/0094048 A1 | 4/2007 | Grichnik |
| 2007/0106533 A1 | 5/2007 | Greene |
| 2007/0106752 A1 | 5/2007 | Moore |
| 2007/0233391 A1 | 10/2007 | Milstein et al. |
| 2007/0239482 A1 | 10/2007 | Finn et al. |
| 2007/0244724 A1 | 10/2007 | Pendergast et al. |
| 2008/0021288 A1 | 1/2008 | Bowman et al. |
| 2008/0046292 A1 | 2/2008 | Myers et al. |
| 2008/0097938 A1 | 4/2008 | Guyon et al. |
| 2008/0131374 A1 | 6/2008 | Medich et al. |
| 2008/0133269 A1 | 6/2008 | Ching |
| 2008/0147441 A1 | 6/2008 | Kil |
| 2008/0172214 A1 | 7/2008 | Col et al. |
| 2008/0172251 A1 | 7/2008 | Reichert et al. |
| 2008/0183454 A1 | 7/2008 | Barabasi et al. |
| 2008/0195422 A1 | 8/2008 | Nessinger et al. |
| 2008/0243548 A1 | 10/2008 | Cafer |
| 2008/0249376 A1 | 10/2008 | Zaleski et al. |
| 2008/0255884 A1 | 10/2008 | Carus et al. |
| 2008/0256006 A1 | 10/2008 | Buscema et al. |
| 2008/0268413 A1 | 10/2008 | Leichner |
| 2008/0275731 A1 | 11/2008 | Rao et al. |
| 2008/0287746 A1 | 11/2008 | Reisman |
| 2008/0288292 A1 | 11/2008 | Bi et al. |
| 2008/0288474 A1 | 11/2008 | Chin et al. |
| 2008/0294692 A1 | 11/2008 | Angell et al. |
| 2008/0301177 A1 | 12/2008 | Doherty |
| 2008/0306926 A1 | 12/2008 | Friedlander et al. |
| 2009/0006431 A1 | 1/2009 | Agrawal et al. |
| 2009/0012928 A1 | 1/2009 | Lussier et al. |
| 2009/0112892 A1 | 4/2009 | Cardie et al. |
| 2009/0125333 A1 | 5/2009 | Heywood et al. |
| 2009/0132284 A1 | 5/2009 | Fey et al. |
| 2009/0164249 A1 | 6/2009 | Hunt et al. |
| 2009/0228303 A1 | 9/2009 | Faulkner et al. |
| 2009/0259493 A1 | 10/2009 | Venon et al. |
| 2009/0299767 A1 | 12/2009 | Michon et al. |
| 2009/0299977 A1 | 12/2009 | Rosales |
| 2009/0304246 A1 | 12/2009 | Walker et al. |
| 2009/0313041 A1 | 12/2009 | Eder |
| 2009/0318775 A1* | 12/2009 | Michelson ............ G06Q 10/00 600/301 |
| 2009/0319295 A1 | 12/2009 | Kass-Hout et al. |
| 2010/0082369 A1 | 4/2010 | Prenelus et al. |
| 2010/0088117 A1 | 4/2010 | Belden et al. |
| 2010/0121883 A1 | 5/2010 | Cutting et al. |
| 2010/0131434 A1 | 5/2010 | Magent et al. |
| 2010/0131438 A1 | 5/2010 | Pandya et al. |

(56) References Cited

U.S. PATENT DOCUMENTS

| | | |
|---|---|---|
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0153133 A1 | 6/2010 | Angell et al. |
| 2010/0179818 A1 | 7/2010 | Kelly et al. |
| 2010/0185685 A1 | 7/2010 | Chew et al. |
| 2010/0198755 A1 | 8/2010 | Soll et al. |
| 2010/0274576 A1 | 10/2010 | Young |
| 2010/0293003 A1 | 11/2010 | Abbo |
| 2010/0299155 A1 | 11/2010 | Findlay et al. |
| 2010/0324861 A1 | 12/2010 | Goulding et al. |
| 2010/0324938 A1 | 12/2010 | Ennett et al. |
| 2011/0010401 A1 | 1/2011 | Adams et al. |
| 2011/0015937 A1 | 1/2011 | Janas et al. |
| 2011/0046979 A1 | 2/2011 | Tulipano et al. |
| 2011/0067108 A1 | 3/2011 | Hoglund |
| 2011/0077973 A1 | 3/2011 | Breitenstein et al. |
| 2011/0087501 A1 | 4/2011 | Severin |
| 2011/0093467 A1 | 4/2011 | Sharp et al. |
| 2011/0119089 A1 | 5/2011 | Carlisle |
| 2011/0161110 A1 | 6/2011 | Mault |
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0016685 A1 | 1/2012 | Ryan et al. |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1* | 3/2012 | McDonald ............... A61B 5/11 600/508 |
| 2012/0086963 A1 | 4/2012 | Fujitsuka et al. |
| 2012/0089420 A1 | 4/2012 | Hoffman et al. |
| 2012/0089421 A1 | 4/2012 | Hoffman et al. |
| 2012/0095780 A1 | 4/2012 | McNair |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | McErlane |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2012/0246102 A1 | 9/2012 | Sudharsan |
| 2013/0006911 A1 | 1/2013 | Christie, IV et al. |
| 2013/0023434 A1 | 1/2013 | Van Laar |
| 2013/0046529 A1 | 2/2013 | Grain et al. |
| 2013/0046558 A1 | 2/2013 | Landi et al. |
| 2013/0110547 A1 | 5/2013 | Englund et al. |
| 2013/0110548 A1 | 5/2013 | Kutty |
| 2013/0132312 A1 | 5/2013 | Lee et al. |
| 2013/0132323 A1 | 5/2013 | Soto et al. |
| 2013/0197938 A1 | 8/2013 | Bayouk et al. |
| 2013/0245389 A1 | 9/2013 | Schultz et al. |
| 2014/0081652 A1 | 3/2014 | Klindworth |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | McNair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0124269 A1 | 5/2017 | McNair et al. |
| 2020/0043612 A1 | 2/2020 | McNair et al. |
| 2020/0335179 A1 | 10/2020 | Stojadinovic et al. |
| 2021/0177338 A1 | 6/2021 | Pagi et al. |

FOREIGN PATENT DOCUMENTS

| | | | |
|---|---|---|---|
| WO | 2006/002465 A1 | 1/2006 | |
| WO | WO-2006002465 A1 * | 1/2006 | ............. G16H 50/80 |
| WO | 2012/122122 A1 | 9/2012 | |
| WO | 2012122195 A1 | 9/2012 | |
| WO | 2012122196 A1 | 9/2012 | |

OTHER PUBLICATIONS

Non-Final Office Action dated Dec. 27, 2017 in U.S. Appl. No. 13/963,732, 18 pages.
Final Office Action dated Jan. 4, 2018 in U.S. Appl. No. 14/147,991, 35 pages.
Final Office Action dated Jan. 5, 2018 in U.S. Appl. No. 14/148,028, 44 pages.
Final Office dated Jan. 18, 2018 in U.S. Appl. No. 14/147,978, 28 pages.
Final Office Action dated Jan. 26, 2018 in U.S. Appl. No. 14/148,039, 33 pages.
Final Office Action dated Feb. 16, 2018 in U.S. Appl. No. 14/281,593, 15 pages.
Non-Final Office Action dated Mar. 2, 2018 in U.S. Appl. No. 14/209,568, 23 pages.
European Search Report dated Mar. 13, 2017 in European Patent Application No. 14835964, 9 pages.
Final Office Action dated May 12, 2017 in U.S. Appl. No. 13/963,732, 20 pages.
Non-Final Office Action dated May 18, 2017 in U.S. Appl. No. 14/147,978, 29 pages.
Non-Final Office Action dated Jun. 6, 2017 in U.S. Appl. No. 14/148,059, 30 pages.
Non-Final Office Action dated Jan. 13, 2017 in U.S. Appl. No. 13/647,187, 20 pages.
Final Office Action dated Feb. 16, 2017 in U.S. Appl. No. 14/175,750, 13 pages.
Kiran, R. Uday, and P. Krishna Re. "An improved multiple minimum support based approach to mine rare association rules." Computational Intelligence and Data Mining, 2009. CIDM'09. IEEE Symposium on. IEEE, 2009.
Final Office Action dated Jun. 16, 2017 in U.S. Appl. No. 14/209,568, 20 pages.
First Action Interview Preinterview Communication dated Jun. 21, 2017 in U.S. Appl. No. 14/281,593, 4 pages.
Non-Final Office Action dated Jun. 21, 2017 in U.S. Appl. No. 14/148,039, 34 pages.
Non-Final Office Action dated Jun. 28, 2017 in U.S. Appl. No. 14/148,028, 31 pages.
Non-Final Office Action dated Jul. 5, 2017 in U.S. Appl. No. 14/147,991, 36 pages.
Non-Final Office Action dated Jul. 24, 2017 in U.S. Appl. No. 14/148,020, 22 pages.
Supplemental Notice of Allowability dated Jul. 26, 2017 in U.S. Appl. No. 14/477,284, 6 pages.
Final Office Action dated Jul. 27, 2017 in U.S. Appl. No. 13/647,187, 23 pages.
Non-Final Office Action dated Jul. 31, 2017 in U.S. Appl. No. 14/148,050, 24 pages.
Non-Final Office Action dated Aug. 10, 2017 in U.S. Appl. No. 14/148,002, 26 pages.
First Action Interview Office Action dated Sep. 6, 2017 in U.S. Appl. No. 14/281,593, 7 pages.
Final Office Action dated Sep. 23, 2016 in U.S. Appl. No. 14/148,059, 27 pages.
Final Office Action dated Sep. 26, 2016 in U.S. Appl. No. 13/269,244, 35 pages.
Final Office Action dated Oct. 3, 2016 in U.S. Appl. No. 14/148,046, 26 pages.

(56) References Cited

OTHER PUBLICATIONS

Final Office Action dated Nov. 2, 2016 in U.S. Appl. No. 13/874,961, 18 pages.
Final Office Action dated Dec. 15, 2016 in U.S. Appl. No. 13/250,072, 18 pages.
Non-Final Office Action dated Sep. 21, 2017 in U.S. Appl. No. 14/148,046, 27 pages.
Non-Final Office Action dated Sep. 22, 2017 in U.S. Appl. No. 14/175,750, 10 pages.
Non-Final Office Action dated Oct. 2, 2017 in U.S. Appl. No. 13/250,072, 8 pages.
First Action Interview Pre-Interview Communication dated Dec. 8, 2017 in U.S. Appl. No. 14/792,736, 22 pages.
Final Office Action dated Dec. 11, 2017 in U.S. Appl. No. 14/148,059, 27 pages.
Final Office Action received for U.S. Appl. No. 12/982,131, dated Apr. 24, 2013, 25 pages.
Final Office Action received for U.S. Appl. No. 14/555,058, dated Sep. 7, 2018, 19 pages.
Final Office Action received for U.S. Appl. No. 14/792,736, dated Oct. 15, 2018, 18 pages.
Non-Final Office Action received for U.S. Appl. No. 12/982,131, dated Dec. 20, 2013, 19 pages.
Non-Final Office Action received for U.S. Appl. No. 14/147,978, dated Sep. 28, 2018, 29 pages.
Non-Final Office Action received for U.S. Appl. No. 14/555,058, dated Dec. 29, 2017, 13 pages.
Non-Final Office Action received for U.S. Appl. No. 14/477,284, dated Aug. 5, 2015, 11 pages.
Notice of Allowance received for U.S. Appl. No. 13/874,961, dated Oct. 15, 2018, 9 pages.
Final Office Action dated Jun. 28, 2016 in U.S. Appl. No. 13/874,961, 19 pages.
Final Office Action dated Jul. 1, 2016 in U.S. Appl. No. 14/147,978, 25 pages.
Final Office Action dated Jul. 14, 2016 in U.S. Appl. No. 14/148,028, 28 pages.
Final Office Action dated Jul. 20, 2016 in U.S. Appl. No. 14/148,039, 32 pages.
Non-Final Office Action dated Jul. 26, 2016 in U.S. Appl. No. 13/963,732, 16 pages.
Final Office Action dated Jul. 29, 2016 in U.S. Appl. No. 14/148,020, 23 pages.
Notice of Allowance dated Aug. 2, 2016 in U.S. Appl. No. 14/477,284, 7 pages.
Final Office Action dated Aug. 15, 2016 in U.S. Appl. No. 14/147,991, 34 pages.
First Action Interview Office Action dated Aug. 17, 2016 in U.S. Appl. No. 14/175,750, 5 pages.
Non-Final Office Action dated Sep. 1, 2016 in U.S. Appl. No. 14/209,568, 12 pages.
Final Office Action dated Sep. 8, 2016 in U.S. Appl. No. 14/148,002, 24 pages.
Final Office Action dated Sep. 9, 2016 in U.S. Appl. No. 14/148,050, 23 pages.
Non-Final Office Action dated Mar. 30, 2016 in U.S. Appl. No. 13/250,072, 12 pages.
Non-Final Office Action dated Mar. 10, 2016 in U.S. Appl. No. 13/269,244, 28 pages.
Final Office Action dated May 3, 2016 in U.S. Appl. No. 13/647,187, 19 pages.
First Action Interview Preinterview Communication dated Mar. 10, 2016 in U.S. Appl. No. 14/175,750, 4 pages.
International Preliminary Report on Patentability dated Feb. 25, 2016 in Application No. PCT/US2014/050735, 9 pages.
First Action Interview Office Action dated Jan. 20, 2016 in U.S. Appl. No. 14/147,991, 8 pages.
First Action Interview Office Action dated Jan. 15, 2016 in U.S. Appl. No. 14/148,002, 8 pages.
First Action Interview Office Action dated Jan. 6, 2016 in U.S. Appl. No. 14/148,020, 8 pages.
First Action Interview Office Action dated Feb. 26, 2016 in U.S. Appl. No. 14/148,046, 8 pages.
First Action Interview Office Action dated Jan. 22, 2016 in U.S. Appl. No. 14/148,050, 8 pages.
Notice of Allowance dated Mar. 11, 2016 in U.S. Appl. No. 14/477,284, 6 pages.
Abbott A, Tsay A. Sequence Analysis and Optimal Matching Methods in Sociology, Review and Prospect. Sociol Meth Res 2000;29:3-33.
Agrawal R, et al. 'Fast Discovery of Association Rules.' In Fayyad U, et al., eds., Advances in Knowledge Discovery and Data Mining, pp. 307-328. Menlo Park, AAAI Press, 1996.
Berchtold A, Raftery A. The Mixture Transition Distribution Model for High-Order Markov Chains and Non-Gaussian Time Series. Stat Sci 2002;17:328-56.
Billari F, et al. Timing, Sequencing, and quantum of Life Course Events: A Machine-Learning Approach. Eur J Pop 2006;22:37-65.
Deville J, Saporta G. Correspondence Analysis with an Extension Towards Nominal Time Series. J Econometrics 1983;22:169-89.
Dijkstra W, Taris T. Measuring the Agreement Between Sequences. Sociol Meth Res 1995;24:214-31.
Dvorak J, et al. Risk Factor Analysis for Injuries in Football Players: Possibilities for a Prevention Program. Am J Sports Med 2000;28:S69-74.
Dvorak J, Junge A. Football Injuries and Physical Symptoms: A Review of the Literature. Am J Sports Med 2000;28:S3-9.
Han J-W, et al. Frequent Pattern Mining: Current status and future directions. Data Mining and Knowledge Discovery 2007;15:55-86.
Hawkins R, Fuller C. A Prospective Epidemiological Study of Injuries in Four English Professional Football Clubs. Br J Sports Med 1999;33:196-203.
Junge A, Dvorak J. Soccer Injuries: A Review on Incidence and Prevention. Sports Med. 2004;34:929-38.
Nielsen A, Yde J. Epidemiology and Traumatology of Injuries in Soccer. Am J Sports Med 1989;17:803-7.
Zaki M. Spade: An Efficient Algorithm for Mining Frequent Sequences. Machine Learning 2001;42:31-60.
Huyse, Frits et al., Compri—An Instrument to Detect Patients With Complex Care Needs; Psychosomatics 42:3, May-Jun. 2001; 7 pages.
Berry, Leonard et al., Care Coordination for Patients With Complex Health Profiles in Inpatients and Outpatient Settings; Mayo Clinic Proceedings; www.mayoclinicproceedings.org; Jan. 11, 2013; 11 pages.
Cohen, Eyal et al., Integrated Complex Care Coordination For Children With Medical Complexity: A Mixed-Methods Evaluation Of Tertiary Care-Community Collaboration; BioMed Central The Open Access Publisher; www.biomedcentral.com/1472-6963/12/366; Oct. 23, 2012; 23 pages.
Nealon, et al.: Agent-Based Applications in Health Care, Department of Computing, Oxford Brookes University and Computer Science and Mathematics Department, University Rovira I Virgill, 17 pages.
Kang, et al.: Mining Based Decision Support Multi-agent System for Personalized e-Healthcare Service*, Schook of Computer Engineering, Sungkyunkwan University, 10 pages.
Mabry, et al.: Clinical Decision Support with IM-Agents and ERMA Multi-agents, Department of Computer Science and Emergency Medicine, 6 pages.
Murat Sariyar and Andreas Borg, The Recordlinkage Package: Detecting Errors in Data, Dec. 2010, The R Journal vol. 212, pp. 61-67.
Christian Roever, Package 'bspec', Feb. 21, 2013, r-project.org. pp. 1-27.
Ohno-Machado, Lucila; "Realizing the full potential of electronic health records: the role of natural language processing", Sep. 2011, Journal of American Medical Information Association, vol. 18 No 5, p. 539.
Aronson, Alan R., "MetaMap: Mapping Text to the UMLS Metathesaurus", 2006, pp. 1-26.

(56) References Cited

OTHER PUBLICATIONS

Final Office action received for U.S. Appl. No. 13/647,187, dated Dec. 14, 2018, 28 pages.
Non-Final Office Action received for U.S. Appl. No. 14/147,991, dated Nov. 27, 2018, 37 pages.
Final Office Action dated Apr. 2, 2018 in U.S. Appl. No. 14/148,020, 21 pages.
Final Office Action dated Apr. 2, 2018 in U.S. Appl. No. 14/148,050, 24 pages.
Final Office Action dated Jun. 13, 2018 in U.S. Appl. No. 14/175,750, 11 pages.
Final Office Action dated May 1, 2018 in U.S. Appl. No. 14/148,046, 31 pages.
Final Office Action dated May 30, 2018 in U.S. Appl. No. 14/148,002, 29 pages.
Final Office Action dated May 31, 2018 in U.S. Appl. No. 13/250,072, 20 pages.
First Action Interview Office Action dated Apr. 17, 2018 in U.S. Appl. No. 14/792,736, 23 pages.
Non-Final Office Action dated Apr. 13, 2018 in U.S. Appl. No. 13/647,187, 27 pages.
Non-Final Office Action dated May 3, 2018 in U.S. Appl. No. 15/392,928, 15 pages.
Non-Final Office Action dated Jun. 28, 2018 in U.S. Appl. No. 14/148,059, 27 pages.
Final Office Action dated Jun. 29, 2018 in U.S. Appl. No. 13/963,732, 22 pages.
Arpaia et al., "Multi-Agent Remote Predictive Diagnosis of Dangerous Good Transports", Instrumentation and Measurement Technology Conference, Proceedings of the IEEE, May 17-19, 2005, pp. 1685-1690.
Non-Final Office Action received for U.S. Appl. No. 14/555,058, dated Jun. 25, 2019, 20 pages.
Non-Final Office Action received for U.S. Appl. No. 13/963,732, dated Jul. 11, 2019, 13 pages.
Non-Final Office Action received for U.S. Appl. No. 14/148,046, dated Jun. 24, 2019, 27 pages.
Final Office Action received for U.S. Appl. No. 14/148,020, dated Oct. 9, 2019, 25 pages.
Preinterview First Office Action received for U.S. Appl. No. 15/855,720, dated Oct. 3, 2019, 4 pages.
Non-Final Office Action received for U.S. Appl. No. 14/148,059, dated Apr. 26, 2019, 28 pages.
Non-Final Office Action received for U.S. Appl. No. 14/792,736, dated Apr. 11, 2019, 18 pages.
Final Office Action received for U.S. Appl. No. 14/555,058, dated Feb. 12, 2020, 22 pages.
First Action Interview Office Action received for U.S. Appl. No. 15/386,876, dated Jan. 28, 2020, 24 pages.
Non-Final Office Action received for U.S. Appl. No. 13/269,244, dated Apr. 8, 2020, 17 pages.
Final Office Action received for U.S. Appl. No. 13/269,244, dated Aug. 12, 2020, 18 pages.
Final Office Action received for U.S. Appl. No. 14/148,059, dated Jul. 16, 2020, 16 pages.
Final Office Action received for U.S. Appl. No. 15/855,720, dated Jul. 2, 2020, 15 pages.
Notice of Allowance received for U.S. Appl. No. 14/148,020, dated Jul. 22, 2020, 10 pages.
Appavoo et al., "Enabling Autonomic Behavior in Systems Software With Hot Swapping", IBM Systems Journal, vol. 42, No. 1, 2003, pp. 60-76.
Townsend, Hilary, "Natural Language Processing and Clinical Outcomes: The Promise and Progress of NLP for Improved Care", Journal of AHIMA, vol. 84, No. 2, Available online at: <https://bok.ahima.org/doc?oid=106198#.X0SgnSgzY2x>, Mar. 2013, 3 pages.
Non-Final Office Action received for U.S. Appl. No. 16/819,890, dated Sep. 29, 2020, 12 pages.
Non-Final Office Action received for U.S. Appl. No. 15/386,876, dated Sep. 14, 2020, 15 pages.
Notice of Allowance received for U.S. Appl. No. 14/148,046, dated Oct. 7, 2020, 11 pages.
The Comprehensive R Archive Network, R, Available online at: <http://cran.r-project.org>, Retrieved on Feb. 27, 2020, 1 page.
Cook et al., "Making Prophecies with Decision Predicates", ACM 978-1-4503-0490-0/11/01, Jan. 2011, 14 pages.
Prados-Suarez et al., "Contextualized Access to Electronical Health Records in Cardiology", IEEE Transactions on Information Technology in Biomedicine, vol. 16, No. 3, doi: 10.1109/TITB.2011.2178033., May 2012, pp. 401-412.
Final Office action received for U.S. Appl. No. 14/555,058, dated Jun. 22, 2021, 12 pages.
Non-Final Office action received for U.S. Appl. No. 16/237,304, dated Jul. 7, 2021, 13 pages.
Non-Final Office Action received for U.S. Appl. No. 16/819,890, dated Jun. 24, 2021, 14 pages.
Notice of Allowance received for U.S. Appl. No. 15/855,720, dated Jun. 1, 2021, 15 pages.
Preinterview First Office Action received for U.S. Appl. No. 16/601,311, dated Jun. 15, 2021, 4 pages.
Shirabad et al., "Implementing an Integrative Multi-agent Clinical Decision Support System with Open Source Software", Journal of Medical Systems 36, Available online at: <https://doi.org/10.1007/s10916-010-9452-9>, 2012, pp. 123-137.
Final Office Action received for U.S. Appl. No. 14/148,039, dated Feb. 1, 2021, 17 pages.
Final Office Action received for U.S. Appl. No. 15/386,876, dated Jan. 11, 2021, 16 pages.
Non-Final Office Action received for U.S. Appl. No. 16/868,642, dated Feb. 4, 2021, 24 pages.
Abernethy et al., "Eliciting Consumer Preferences Using Robust Adaptive Choice Questionnaires", IEEE Transactions on Knowledge and Data Engineering, vol. 20, No. 2, Feb. 2008, pp. 145-155.
Othman et al., "Agent Based Preprocessing", International Conference on Intelligent and Advanced Systems 2007, 2007, pp. 219-223.
Ta et al., "Data Descriptor: Columbia Open Health Data, Clinical Concept Prevalence and Co-occurrence from Electronic Health Records", Scientific data, vol. 5, 180273, doi: 10.1038/sdata.2018.273, Nov. 27, 2018, pp. 1-17.
Uhrmacher et al., "Distributed, Parallel Simulation of Multiple, Deliberative Agents", Proceedings of the fourteenth workshop on Parallel and distributed simulation, May 2000, pp. 101-108.
Summons to Attend Oral Proceedings received for European Patent Application No. 14835964.9, mailed on Jan. 13, 2021, 12 pages.
Notice of Allowance received for U.S. Appl. No. 16/588,647, dated Apr. 1, 2021, 21 pages.
Final Office Action received for U.S. Appl. No. 14/209,568, dated Jul. 12, 2021, 9 pages.
Duff, SI. , "Development and history of sparse direct methods", SIAM Conference on Applied Linear Algebra, Available online at: <http://www,numerical.rl.ac.uk/people/isd/isd,html>, Oct. 26-29, 2009, 44 pages.
Xue et al., "Fast Query by Example of Environmental Sounds via Robust and Efficient Cluster-based Indexing", 2008 IEEE, International Conference on Acoustics, Speech and Signal Processing, Available online at: <doi: 10.1109/ICASSP.2008.4517532>, 2008, pp. 5-8.
Pre-Interview First Office action received for U.S. Appl. No. 17/011,474, dated Sep. 28, 2021, 4 pages.

\* cited by examiner

*FIG. 6A*

| ID | POS | AGEGRP | FIRSTINJPART | WKFIRSTINJ | W.01 | W.02 | W.03 |
|----|-----|--------|--------------|------------|------|------|------|
| 25 | gk  | 36+    | add          | 11         | fit  | fit  | fit  |
| 26 | def | 21-25  | ank          | 3          | fit  | fit  | ank  |
| 27 | mid | 21-25  | ank          | 14         | fit  | fit  | fit  |
| 28 | def | 21-25  | kne          | 5          | fit  | fit  | fit  |
| 30 | mid | 31-35  | tib          | 3          | fit  | fit  | tib  |
| 38 | mid | 21-25  | fib          | 20         | fit  | fit  | fit  |
| 42 | fwd | 21-25  | ank          | 11         | fit  | fit  | fit  |
| 43 | mid | 31-35  | tib          | 14         | fit  | fit  | fit  |
| 57 | def | 31-35  | kne          | 9          | fit  | fit  | fit  |
| 62 | mid | 31-35  | fem          | 17         | fit  | fit  | fit  |
| 63 | def | 31-35  | fem          | 10         | fit  | fit  | fit  |

FIG. 6B

```
# DSM 08-DEC-2012
# statistical trajectory mining to discover significant longitudinal patterns in 2012 pro-
soccer dataset
# lower-extremity injury sequences in 286 players with 2 or more lower-extremity injuries
during 2012

library("TraMineR")
library("cluster")

transfer data.frame from dsm_mls_2012_multiple_lower_extremity_injuries.xlsx represent injured body parts in anatomical distal-to-proximal order
mls.alphab <- c("toe","foo","ank","tib","fib","kne","pat","fem","gle","add","hip","fit")

# generate state-sequences from data frame
mls.seq <- seqdef(dsm_MLS_traminer, 6:57, xtstep=12, alphabet=mls.alphab)

# generate state-sequence distance array using seqsubm build method transition-rate
"TRATE"
# and substitution-cost matrix optimal-matching "OM" algorithm
mls.om <- seqdist(mls.seq, method="OM", indel=1, sm="TRATE")
# mls.om <- seqdist(mls.seq, method="OM", indel=1, sm=scost)

# generate statistically most significant top 5 clusters using distance array
mls.clusters <- agnes(mls.om, diss=TRUE, method="ward")
mls.clus5 <- cutree(mls.clusters, k=5)

# plot state-distributions by cluster
clus5.lab <- factor(mls.clus5, labels=paste("Injury Pattern Cluster", 1:5))
seqdplot(mls.seq, group=clus5.lab, border=NA)

# discern degree of pattern disorder between groups
# note: there is no significant relationship of entropy to position or first-injured body part
entropies <- seqient(mls.seq)
lm.ent <- lm(entropies ~ AgeGrp + WkFirstInj, dsm_MLS_traminer)
summary(lm.ent)

```

.
.
.

CONTINUES IN FIG. 7B

*FIG. 7A*

CONTINUES FROM FIG. 7A

.
.
.

```
# Coefficients:
#              Estimate    S.E.    t-value  Pr(>|t|)
# (Intercept)  0.2324263  0.0213   11.1     < 2e-16 ***
# AgeGrp31-35  0.0492044  0.0242   2.02     0.0442 *
# WkFirstInj  -0.0034028  0.0006  -5.55     6e-08 ***

# Residual standard error: 0.096 on 280 degrees of freedom
# Multiple R-squared: 0.124,    Adjusted R-squared: 0.108
F-statistic: 7.896 on 5 and 280 df,  p-value: 5.6e-07 plot state-frequency for top 10 injury patterns in order of frequency of pattern grouped by position
seqfplot(mls.seq, weighted=TRUE, border=NA, withlegend="right", title="Weighted frequencies", group=dsm_MLS_traminer$Pos)

# plot representative trajectory sets grouped by position
# using the default frequency criterion
seqrplot(mls.seq, dist.matrix=mls.om, group=dsm_MLS_traminer$Pos, border=NA)

# plot injury-sequence entropy-index grouped by position
seqplot(mls.seq, type="Ht", group=dsm_MLS_traminer$Pos, border=NA)

# plot mean-time in injured states grouped by position
seqmtplot(mls.seq, group=dsm_MLS_traminer$Pos, ylim=c(0, 30), border=NA)
# tabulate mean-time by injured body part by position
by(mls.seq, dsm_MLS_traminer$Pos, seqmeant)

# calculate body part A to body part B transition rates for sequentially injured part pairs
mls.trate <- seqtrate(mls.seq)
round(mls.trate, 3)

# calculate state frequencies by week
seqstatd(mls.seq[,1:52])

# calculate medoid cluster sequences predicting characteristic patterns of injury
medoid <- seqrep(mls.seq, dist.matrix=mls.om, criterion="dist", nrep=1)
print(medoid, format="SPS")
```

FIG. 7B

DISCOVERING CONTEXT-SPECIFIC SERIAL HEALTH TRAJECTORIES

CROSS-REFERENCE TO RELATED APPLICATIONS

This application is a divisional of U.S. patent application Ser. No. 14/175,750, filed Feb. 7, 2014, entitled "Discovering Context-Specific Serial Health Trajectories," which claims priority to U.S. Provisional Application No. 61/762,178, entitled "DISCOVERING CONTEXT-SPECIFIC SERIAL HEALTH TRAJECTORIES," filed Feb. 7, 2013. The aforementioned applications are hereby incorporated by reference herein.

INTRODUCTION

In many contact sports, contact that arises during competition and practice and the explosive running and frequent change of direction that the sport entails combine to produce a high risk of injury.

By way of illustration, the epidemiology of soccer injuries has been the subject of many published research studies, but virtually all studies examine each injury in isolation from other injuries. To date, no one has investigated whether there are characteristic sequences of injury types or anatomical locations, nor has anyone investigated whether, if such sequences do exist, they are statistically associated with factors that might lead to meaningful, effective prevention. Partly, the lack of studies of this sort is due to the difficulty in examining sequences of events statistically. The statistical methods for measuring clusters of event sequences are only about 20 years old, and the methods are familiar to only a few people—virtually no one in sports medicine or kinesiology.

Since it is well-known that players with previous injury do run an increased risk of reinjury, it is de rigeur to suggest that the injured player should receive some sort of preventive intervention. However, to date the preventive maneuvers are very non-specific and involve player (re-)education, monitoring, performing general strength-training and range-of-motion exercises, and temporizing until the return-to-play decision is made. The preventive maneuvers focus primarily on the body part that sustained the original injury and are agnostic about the interconnections between body parts and biomechanical interactions involved in force-development and alterations in moments about other joints.

But in many sports, certain anatomical sites different from the original injury site are at greater risk subsequent to a particular injury. It is plausible that weakness or other biomechanical compromise at the site of original injury—or pain associated with, or psychological apprehension resulting in the guarding or the protecting of, the previously injured body part, or other factors—may alter the patterns of movement and stresses upon other body parts, in causative or predisposing manner such that other parts experience higher injury rates and/or more severe injuries. Specific preventive interventions that will be most effective in averting injury at the sites that carry that increased risk, but to date it has not been practical to identify which athletes should receive which interventions. Addressing these questions requires discovering whether there are statistically significant trajectories (sequences of serial injuries)—patterns for which context- or trajectory-specific preventive interventions might be designed.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Systems, methods, and computer-readable media are provided for injury characterization, and for detecting matches of an individual subject's record (such as an athlete's record) with collections of other subjects (or athlete's) records, with on serial, longitudinal patterns (time series "trajectories"). For example, some embodiments facilitate the automatic, algorithm-guided ascertainment of record matches between (a) one player's attributes and cumulative longitudinal pattern of serial injuries and (b) a plurality of other players' longitudinal injuries records in a collection of online records that are stored in a computer system. In this way, some embodiments can facilitate athletic training, preventive and rehabilitation medicine, and risk management in athletics.

In one aspect, time series are formed by (a) electronically representing and storing information pertaining to successive longitudinal episodes of injury and the circumstances in which the injuries were incurred; (b) calculating time-series K-nearest-neighbor clusters (or similar clusters) and distances for each such combination; (c) determining the cluster to which a given candidate player injury record is nearest or belongs to; and (d) prescribing one or more interventions that are specific to the plurality of hazards that are characteristic of trajectories that are members of that cluster and that are deemed to be relevant to reducing or mitigating those hazards and thereby are efficacious in preventing subsequent injuries that are prevalent in that trajectory cluster.

In one aspect a method is provided for identifying temporal trajectory clusters in a longitudinal time series database comprised of a plurality of records arranged in rows and columns. The method comprises: assigning a unique identifier to all records in the database; retrieving the date-time stamps associated with each injury episode record and return-to-play; creating a blocking subset of between 1 and all of the columns in the database (variables such as position-played, age, cumulative hours-played, formation or system played and that played by the opponent's team in exposures during which the injury occurred); calculating the entropy index values of each injuries time series retrieved; calculating a plurality of K-nearest-neighbor clusters of the retrieved injury time series records; and calculating trajectory distances between an individual player's record and the centroids of each of the clusters. In an embodiment, a pair-wise matching algorithm is applied for matching a candidate record X against the clusters thus identified, by comparisons of distances and entropies against heuristic threshold values. In an embodiment, the candidate matches are ranked in distance order.

BRIEF DESCRIPTION OF THE DRAWINGS

Embodiments are described in detail below with reference to the attached drawing figures, wherein:

FIGS. 6A and 6B provide depictions of time-series of lower-extremity injuries for athletes, by week, for a fifty-two-week window;

FIGS. 7A and 7B illustratively provide one example embodiment of a computer program routine for facilitating trajectory mining.

DETAILED DESCRIPTION

Figure 1A:
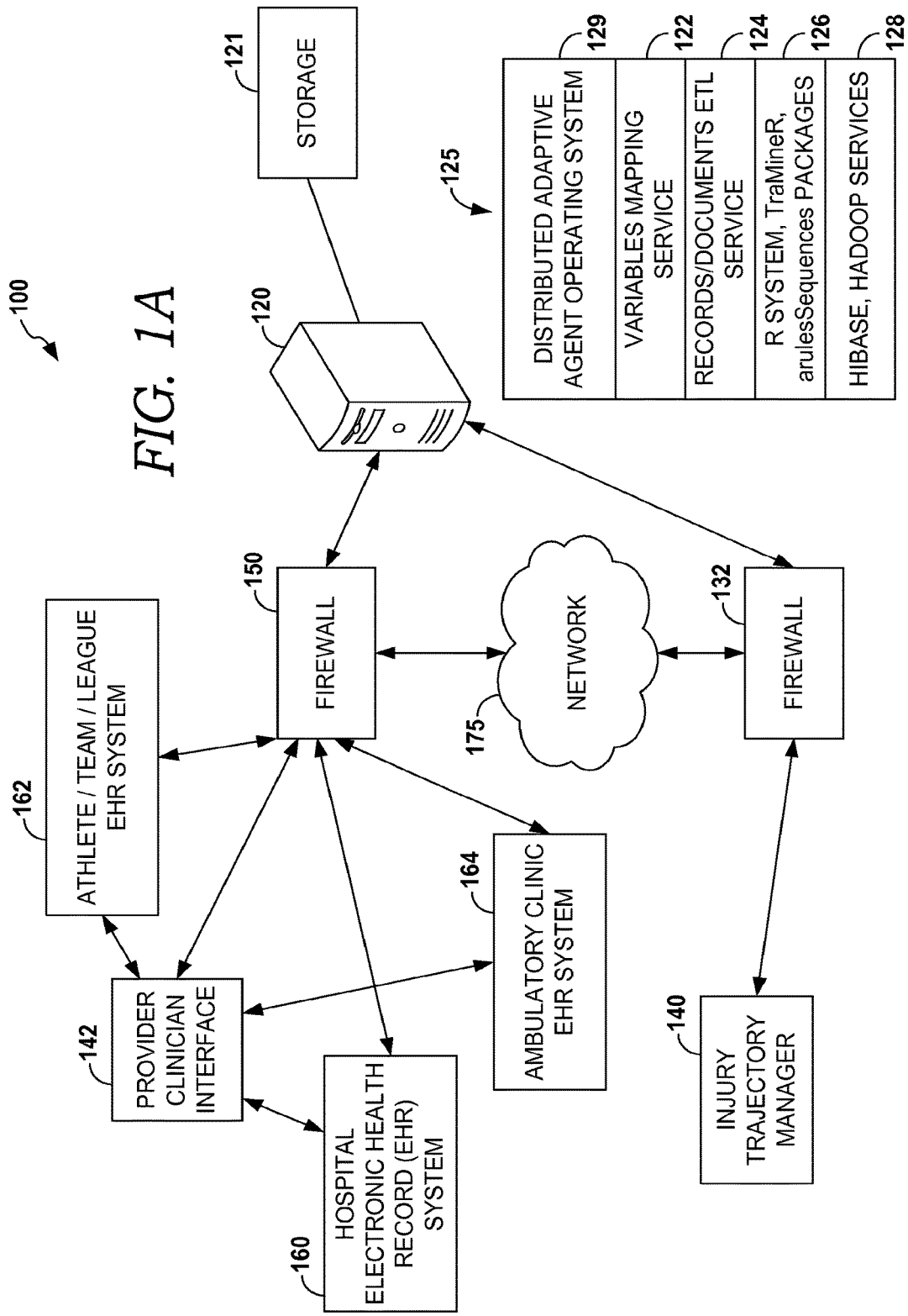
FIGS. 1A and 1B depict block diagrams of aspects of an exemplary operating environment suitable to implement an embodiment of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently.

Embodiments of the invention are directed to methods, computer systems, and computer-readable media for injury characterization, and for detecting matches of an individual subject's record (such as an athlete's record) with collections of other subjects (or athlete's) records, with on serial, longitudinal patterns (time series "trajectories").

Other attempts or efforts at characterizing injury are deficient due to: (1) excessive false-negative rate (false misses), associated with neglecting time series information regarding serial sequences or trajectories of multiple injuries sustained over a period of time; (2) excessive false-positive rate (false hits), commonly arising due to consideration only of individual anatomical structures or other attributes and neglecting distinguishing features contained in time series information; and (3) failure to take into account empirical associations or causative relationships between one or more injured anatomical structures and (a) the biomechanics of adjoining structures and (b) compensatory mechanical or psychological effects on the coupled structures status-post injury.

Accordingly, it is therefore highly valuable and highly desirable to provide embodiments of the methods and systems described herein, for longitudinal multi-injury trajectory classification that takes advantage of time-oriented information, such as information that is readily available for each of the records in the repository and for any new record for which a match in the repository is sought.

Moreover, while a considerable number of studies have described the incidence and injury pattern (injury type, localization, and severity) in each sport, much less is known about risk factors or injury mechanisms. The majority of the injuries are thought to be random, resulting from chance or an error by the player injured or another player. Some players experience only one or a few serial injuries during a season, while other players experience a large number of serial injuries. Some players experience injuries whose duration is short even if the injuries arise frequently, and these players accumulate relatively little time on the injured list. By contrast, other players experience injuries whose resolution takes a long time, with correspondingly long cumulative injured-list days.

Accordingly, some embodiments of the present invention comprise a statistical and computational system and method for inferring clusters of similar sequences or trajectories of serial injuries and for matching individual players' patterns to patterns represented by cluster members based on nearest-neighbor trajectory distances and trajectory disorder ("entropy index") values.

In some aspects, sequence or trajectory cluster discovery can perceived as statistical association discovery over a temporal database. While association rules discover only intra-event patterns (e.g. frequent itemsets), we now also have to discover inter-event patterns (e.g. frequent sequences or trajectories).

Various algorithms considered for mining sequential pattern information are unable scale well with increasing sequence length and database size. The search space is extremely large. For example, with m attributes there are $O(m^k)$ potentially frequent sequences of length k. With hundreds to many thousands (or millions, in the case of collegiate or secondary-school athletics) of objects in a database, the problem of I/O minimization becomes paramount. However, algorithms that are iterative in nature would require as many full database scans as the longest time series sequence.

Turning now to FIG. 1A there is presented an example operating environment 100 suitable for practicing embodiments of the invention. Example operating environment 100 includes a computerized system for compiling and running an embodiment of an injury characterization decision support recommendation service. With reference to FIG. 1A, one or more electronic health record (EHR) systems such as hospital EHR system 160, ambulatory clinic EHR system 164, and athlete/team/league EHR system 162 are communicatively coupled to network 175 and computer system 120, behind a firewall 150. In an embodiment, network 175 includes the Internet, a public network, or a private network.

Example operating environment 100 also includes a firewall 132 between injury trajectory manager 140, computer system 120, and network 175. Although environment 100 includes firewalls 150 and 132, it is contemplated that some operating environments may not have firewalls. In embodiments having a firewall, the firewall may reside on a component between the component and network 175, such as on a server (not shown) or may reside on the component. Thus, in some embodiments, firewall 150 or 132 may comprise a separate firewall associated with each component (or some components) shown communicatively coupled to the firewall.

Embodiments of electronic health record (EHR) systems 160, 162 and 164 include one or more data stores, such as data store 125, of health records and may further include one or more computers or servers that facilitate the storing and retrieval of the health records. Firewall 150 may comprise a separate firewall associated with each EHR system, in some embodiments. Furthermore, in some embodiments, one or more EHR systems 160, 162 and 164 may be located in the cloud or may be stored in data stores that are distributed across multiple physical locations. In some embodiments, EHR systems 160, 162 and 164 further include record systems which store real-time or near real-time patient information, such as wearable, bedside, or in-home patient monitors, for example.

Example operating environment 100 further includes provider clinician interface 142 communicatively coupled to the one or more EHRs 160, 162, and 164. Embodiments of interface 142 may take the form of a user interface operated by a software application or set of applications on a client computing device such as a personal computer, laptop, smartphone, or tablet computing device. In one embodiment, the application(s) includes the PowerChart® solution suite, manufactured by Cerner Corporation. In one embodiment, the application(s) is a Web-based application or applet. Provider clinician interface 142 facilitates accessing and receiving information from a user or health care provider about a specific athlete (or patient) or set of athletes (or patients) for which injury characterization is to be performed and facilitates the display of results, recommendations or orders, for example. In some embodiments interface 142 also facilitates receiving orders for the athlete (or patient), from the clinician/user, based on the results. For example, interface 142 might display results to a user indicating that a given athlete is significantly more likely to suffer a particular injury, given a previously occurring injury and given that player's playing position, and display recommendations for treatment or facilitate receiving instructions for care.

Example operating environment 100 further includes computer system 120, which may take the form of a server, which is communicatively coupled through firewall 150 to EHR systems 160, 162, and 164, and also through firewall 132 to injury trajectory manager 140.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as a local client and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

In an embodiment, injury trajectory manager 140 may take the form of one or more software applications operating on one or more mobile computing devices, tablets, smartphones, front-end terminals in communication with back-end computing systems, laptops or other computing devices. In some embodiments, injury trajectory manager 140 includes a Web-based application or collection of applications that is usable to manage services provided by embodiments of the invention. In some embodiments, manager 140 facilitates calibration, evaluation, re-testing or tailoring, and in some embodiments, manager 140 facilitates receiving feedback information.

Embodiments of computer system 120 include computer software stack 125, which in one embodiment operates in the cloud, as a distributed system on a virtualization layer within computer system 120. Embodiments of software stack 125 include an operating system, such as distributed adaptive agent operating system 129, which may be implemented as a platform in the cloud. In an embodiment, operating system 129 is capable of hosting a number of services such as 122, 124, 126, and 128. Embodiments of services 122, 124, 126, and 128 run as a local or distributed stack in the cloud, on one or more personal computers or servers such as 120, and/or a computing device running manager 140. In one embodiment, manager 140 operates in conjunction with software stack 125.

In embodiments, variables indexing service 122 and Records/Documents ETL service 124 provide services that facilitate retrieving frequent item sets, extracting database records, and cleaning the values of variables in records. In some embodiments, these services invoke software services 126. Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including TraMineR or similar services for facilitating trajectory mining, and arulesSequences or similar services for facilitating operations such as K-nearest neighbor distance calculations. In an embodiment, software services 126 are associated with services 128, which include Apache Hadoop and Hbase framework, or similar frameworks operable for providing a distributed file system.

Example operating environment 101 also includes data store 121, which in some embodiments includes athlete or patient data and information for multiple athletes (or patients); variables associated with athlete or patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers, and other similar information; patient-derived data; and health care provider information, for example. In some embodiments, data store 121 comprises the data stores associated with the one or more EHR systems, such as 161, 162, and 164, and injury trajectory manager 140. Further, although depicted as a single data store, data store 121 may comprise one or more data stores, or may be in the cloud.

Figure 1B:
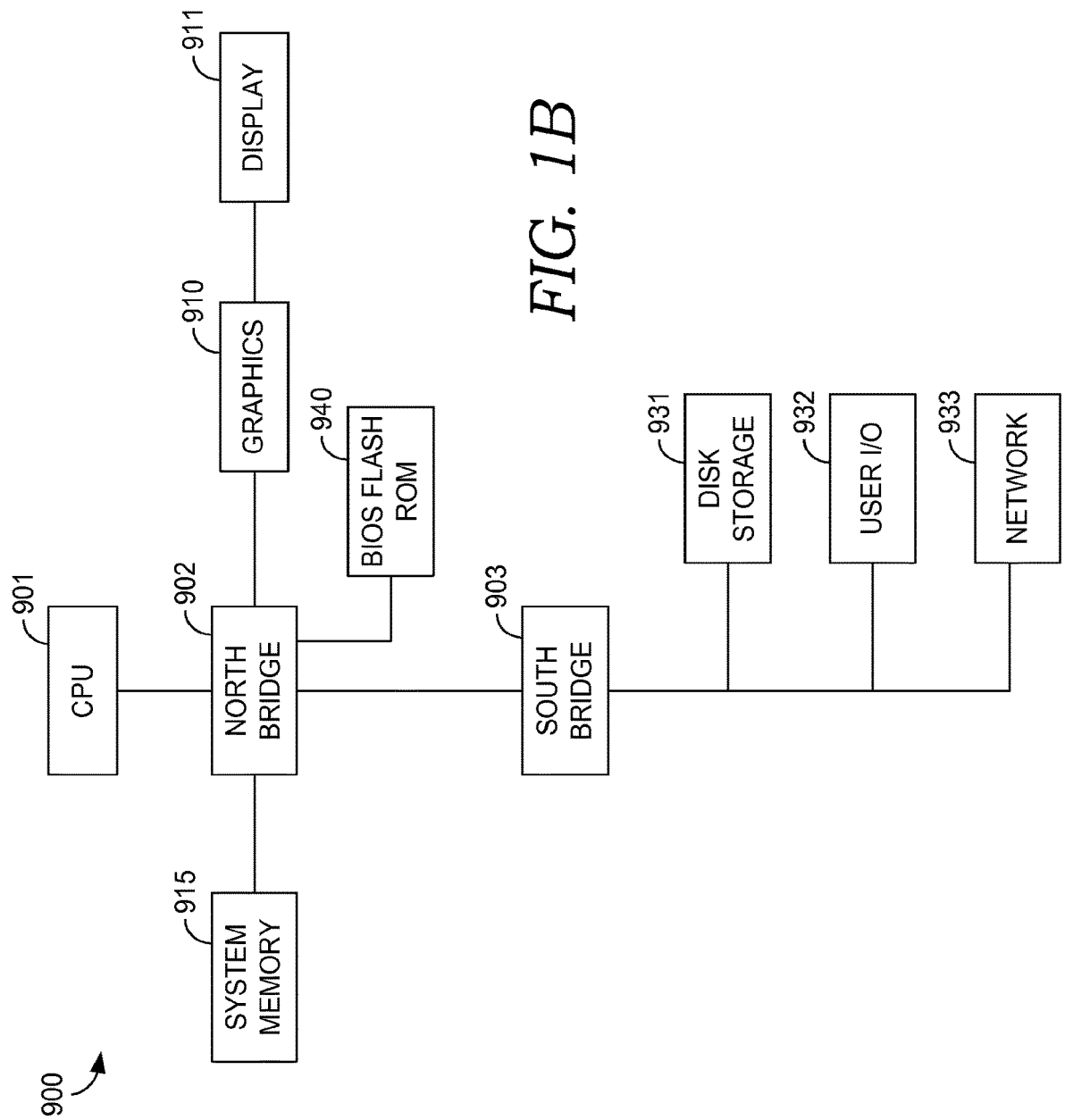

Turning briefly to FIG. 1B, there is shown one example embodiment of computing system 900 that has software instructions for storage of data and programs in computer-readable media. Computing system 900 is representative of a system architecture that is suitable for computer systems such as computer system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In an embodiment, computer system 120 includes an adaptive multi-agent operating system, as described above, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2:
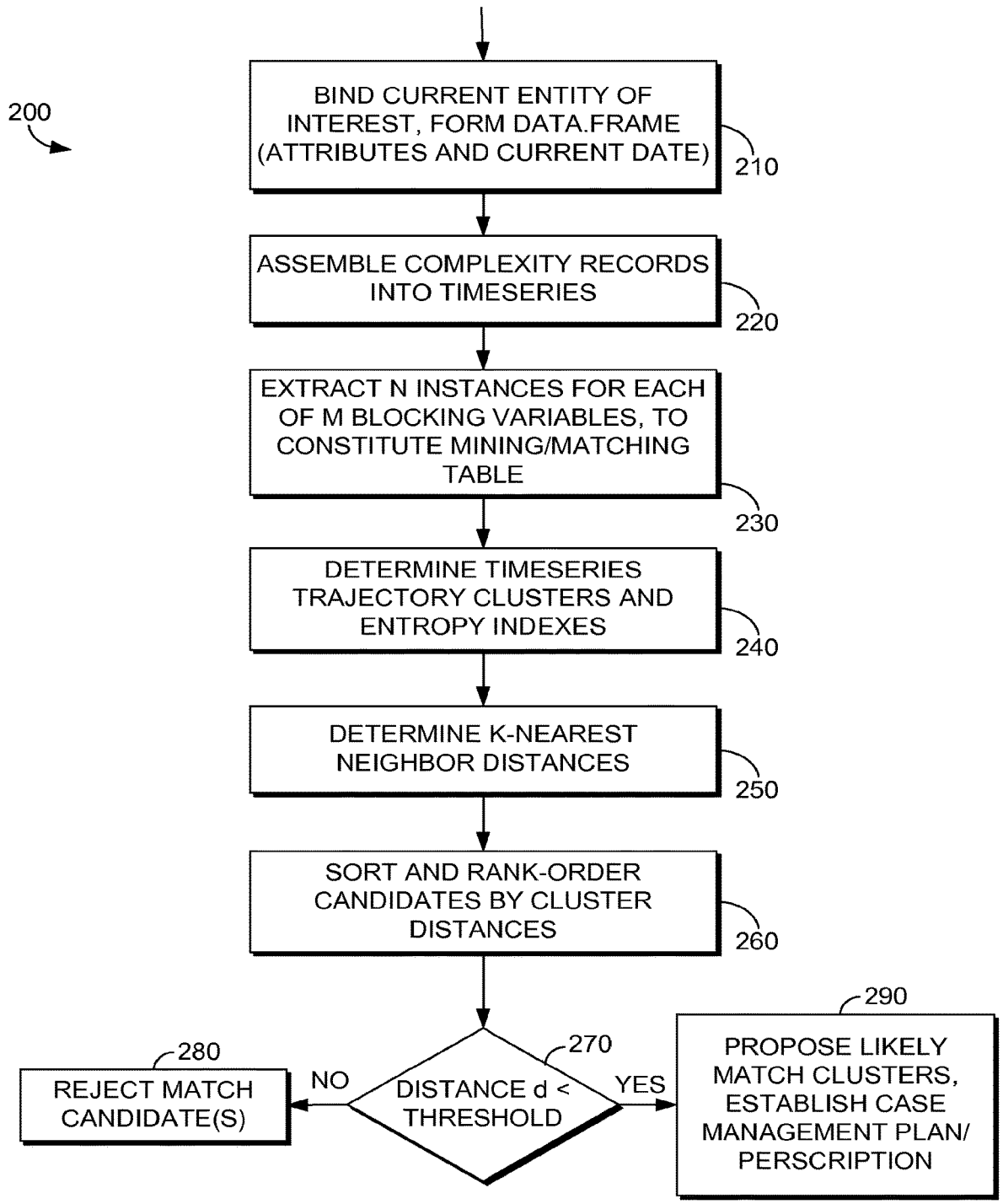
FIG. 2 depicts a flow diagram of a method for characterizing injury in accordance with an embodiment of the invention.

Turning now to FIG. 2, a flow diagram is provided for an embodiment of a method for injury characterization and detecting matches of an individual subject's injury record with collections of other subjects' records having serial, time series trajectories, and referred to generally herein as method 200. A trajectory implies a potential change or potential longitudinal alteration from one condition or state of a property to another condition, and may be viewed as a longitudinal sequence (or pattern) of states. Accordingly, an objective in some embodiments is to compare a first athlete's attributes and longitudinal patterns against other athletes attributes and longitudinal patterns in order to determine the cluster(s) in which the first athlete attributes and longitudinal patterns best fit.

With reference to FIG. 2, some embodiments of the invention use a vertical identification-list ("id-list") database format, wherein associated with each sequence are a list of players in whom the sequence occurs, along with their time-stamps. In these embodiments, all frequent sequences can be enumerated via simple temporal joins (or intersections) on id-lists. Additionally, some embodiments use a sparse-matrix approach to decompose the original search space (lattice) into smaller pieces (sub-lattices) which can then be processed independently, either in main-memory on a single processor or in distributed memory on multiple parallel processors. In this manner, embodiments previously requiring three database scans, require only a single scan with some pre-processed information, thus minimizing I/O costs. In some embodiments, the problem decomposition is decoupled from the pattern search. Thus some embodiments utilize two different search strategies for enumerating the frequent sequences within each sublattice: breadth-first and depth-first search, according to algorithms that are known to those practiced in the art.

At a step 210 of method 200, bind the current entity of interest. In embodiments, the entity of interest is the entity for which it is desired to find other matching entities in a target system. For example, the entity of interest may represent the injury or health record(s) of person or object for which candidate matches are sought, such as an individual athlete or a set (plurality) of athletes. In embodiments, information specifying a patient (athlete) or set of patients (athletes) may be received from a user such as a clinician, health care provider, trainer, or manager, or received from a computer program, such as from a software agent. In some embodiments, a batch process is used to identify the patient (athlete) or set of patients (athletes). In some embodiments, step 210 includes identifying attributes and date information associated with the entity of interest, such as for example, player position, age, specific injury type, date of first injury, date(s) of subsequent injuries, durations of injuries, current date, other EHR information, and other attributes that may be used for determining a trajectory cluster. Further, in some embodiments, the information of step 210 is formed into a data.frame, which is a special data type in the R-system that may include embedded arrays.

At a step 220, the records (including portions of records), such as injury records, patient records, or other complex records, are assembled into a timeseries format. In some embodiments, this includes injury records and other factors such various attributes identified in step 210. An illustrative depiction of example timeseries is provided in FIGS. 6A and 6B. In some embodiments, the records, date, and attribute information are assembled into R-system data.frame data types. So for example, injury records comprising a 52-long row vector, such as shown in FIG. 6A, would be a component of a data.frame.

Figure 6A:
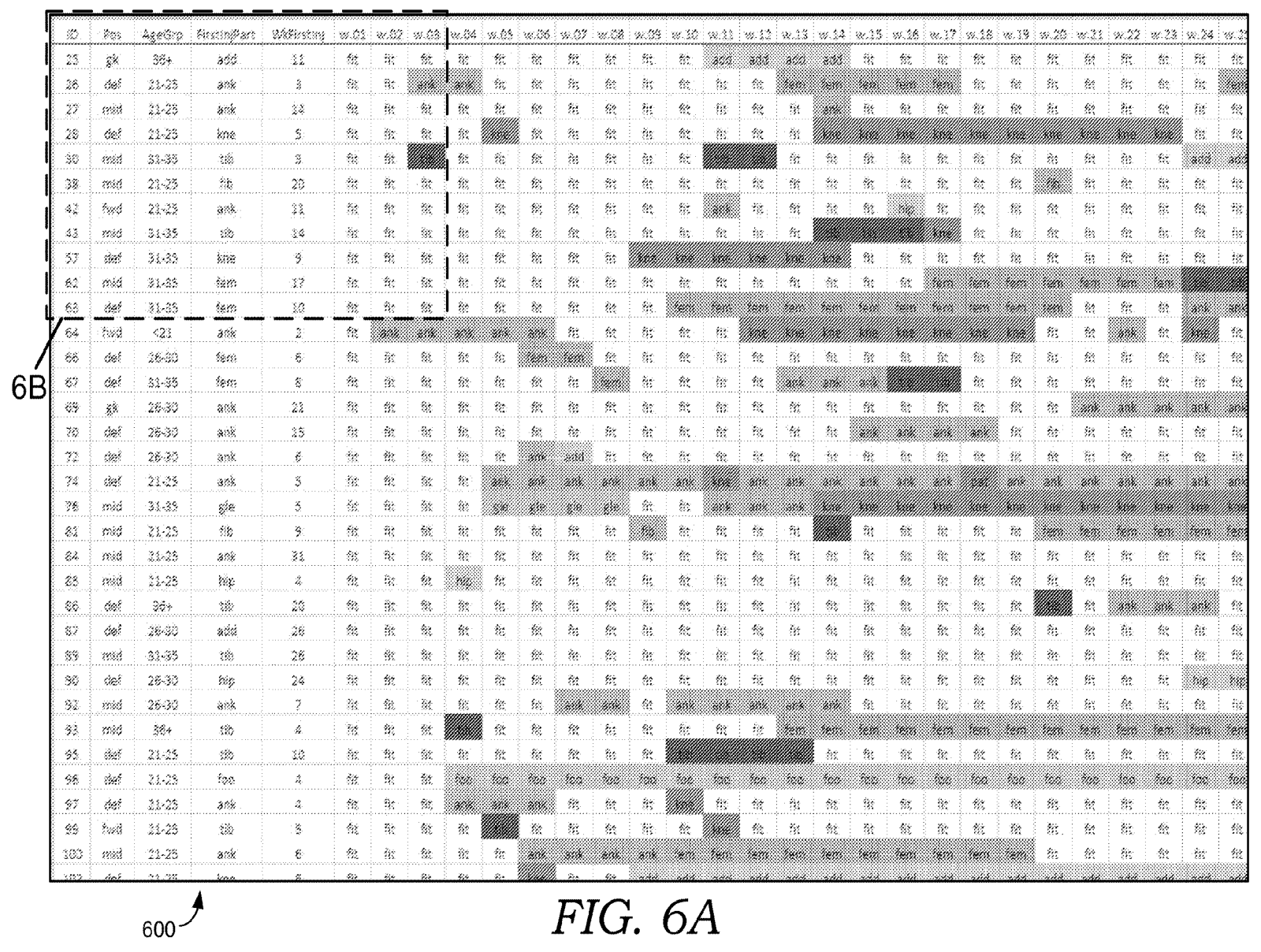

Turning briefly to FIGS. 6A and 6B, an illustrative chart of time-series of lower-extremity injuries for athletes, by week for a fifty-two week window, is provided and referred to generally as 600. Each row of chart 600 corresponds to a player, each column w.01 through w.52 (not shown) corresponds to a week of time. Shaded or colored cells indicate presence of particular injury for that player during that week and the particular injury such as ankle ("ank") foot ("foo"), femur ("fem"), knee ("kne"), patella ("pat"), etc. The left-hand side of chart 600 shows player ID, and some attributes such as play-position (e.g., defender ("def"), mid fielder ("mid"), forward ("fwd"), etc.), age, first injured part ("FirstInjPart"), and week first injured ("WkFirstInj"). In this particular example illustration of the timeseries information, the player information represents de-identified player data from approximately 600 professional soccer players suffering over 5000 injuries over the 2012 season. As shown, most players suffer from at least one injury per year, but many have more than one injury, which are often the result of the first injury. For example, a player with a hurt ankle may overcompensate to protect the ankle thereby injuring his or her hip. FIG. 6B shows a close-up of a portion of the same information illustratively provided in FIG. 6A.

Returning to FIG. 2, at a step 230, for each M blocking variables, N instances are extracted to constitute a candidate trajectory mining/matching table, where M and N are integers greater than or equal to zero. In embodiments, step 230 includes selecting or identifying one or more independent demographic variables that are present in both a reference system and the target system associated with each entity, that are to be used as 'blocking' variables. Blocking variables can include variables such as age, first injury, sport played or player-position, or may also include variables in a specific context, such as whether the athlete or patient has other specific conditions, for example. In some embodiments, blocking variables may be used to determine how data sets are retrieved, when dealing with large-demographic data sets. Continuing with step 230, in some embodiments, from the target system, database records are extracted which contain lexically similar values for the selected blocking variables' values. In embodiments, the extraction is based on factors or attributes identified in step 210. Put another way, filter criteria for the extraction includes the entity of interest and the attributes of the entity that are of interest. In some embodiments, this is facilitated using a hash table to establish the degree of similarity for retrieval.

In some embodiments, for each entity retrieved from the extraction, extract the date-time coordinates for the episodes that the retrieved records represent; compute inter-episode time intervals that separate the records in time; and assemble the intervals as time series associated with each record. In some embodiments, this time series comprises elements representing the time interval between episodes. For example, a simple time series might include numbers representing the number of weeks, days, or hours between episodes.

At a step 240, timeseries trajectory clusters are determined. In embodiments, timeseries trajectory clusters are computed using software services 126, such as the TraMineR package, as described in connection to FIG. 1A. One example embodiment of a computer program routine for trajectory mining is illustratively provided in FIGS. 7A and 7B. A trajectory-mining statistical algorithm as implemented by software services 126, such as the example embodiment shown in FIGS. 7A and 7B, can automatically discover certain 'clusters' of trajectories that are quantitatively prevalent or frequent enough to characterize the injury patterns and transitions from one injury to subsequent injuries. An embodiment of step 240 can produce stable clusters or subsets of clusters, which demographically, in terms of entity specification, have similar longitudinal sequence (or pattern) of states. Thus in some embodiments, step 240 comprises computing a multi-cluster math model and extracting cluster assignment from model results for each entity of interest. An illustrative example of clusters generated by step 240 is provided in FIGS. 3A-3C, which are described below.

In some embodiments, step 240 also determines entropy indexes. Illustrative examples of entropy indexes are provided in FIGS. 5A through 5C. In some embodiments, software services 126, such as the TraMineR package, output optionally individual or summary statistics or a timeseries from which a clinician or caregiver might look at slopes, rates of change, accelerations, or other properties.

Figure 5A:
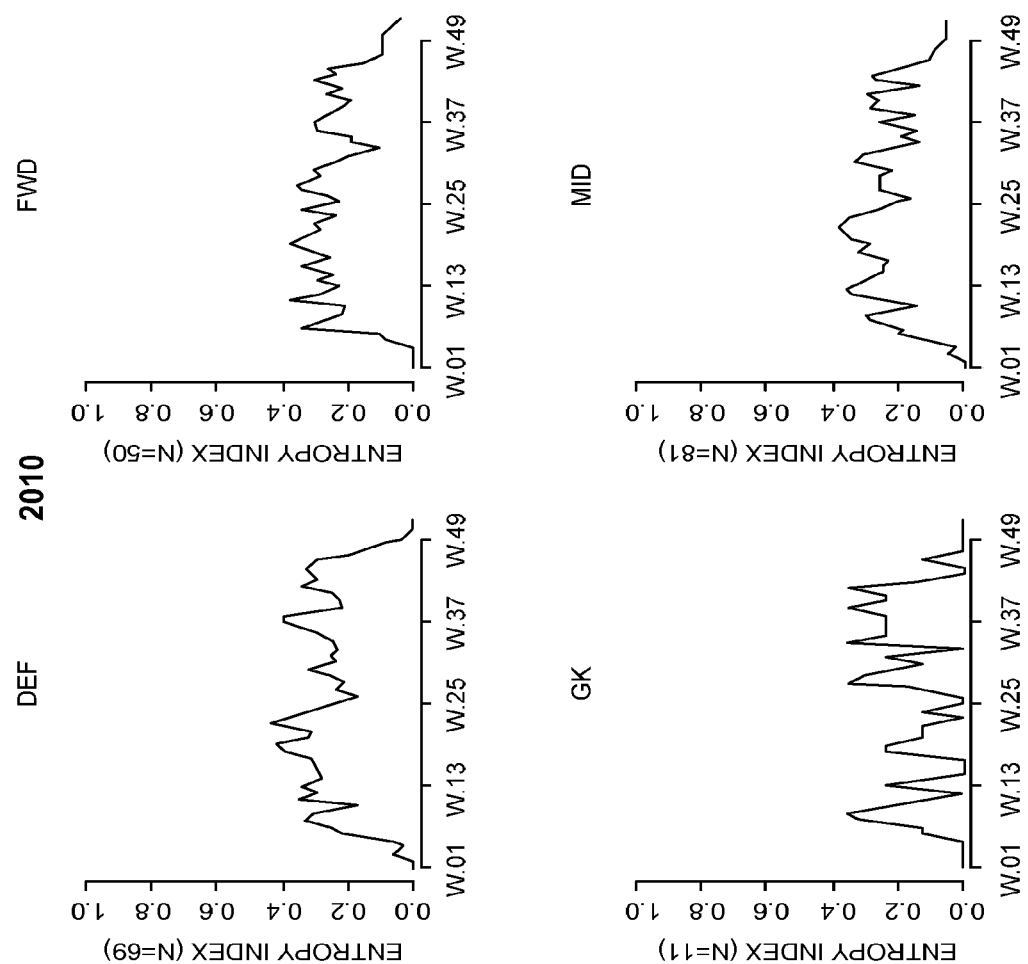
FIGS. 5A-5C depict entropy indices by player-position of serial lower-extremity injuries.
Figure 5B:
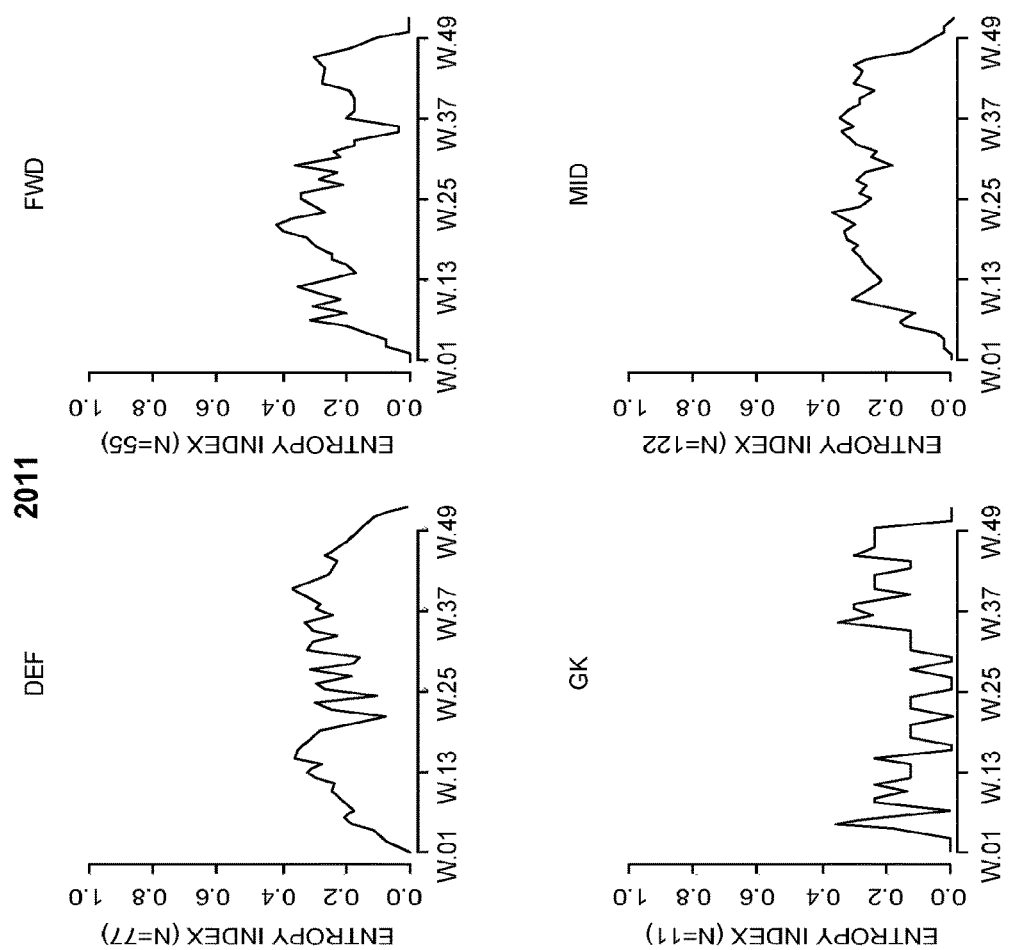
Figure 5C:
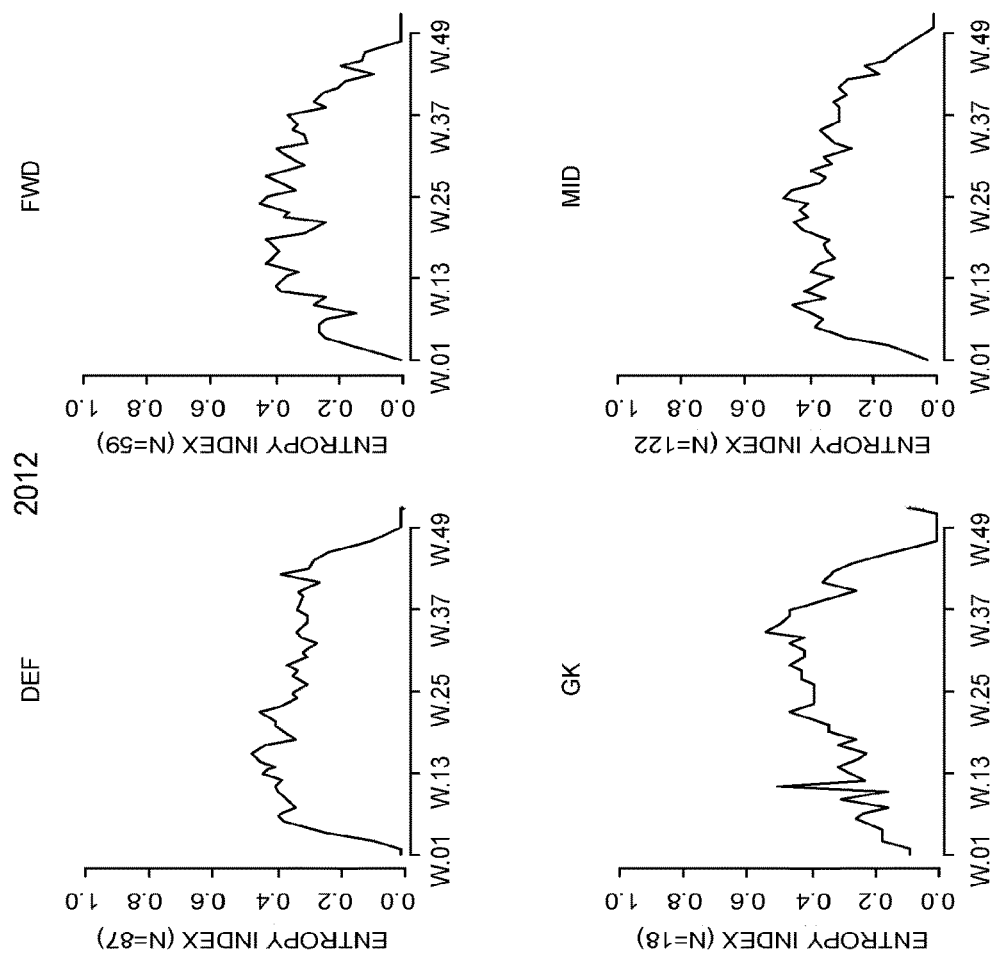

With reference to FIGS. 5A-5C, entropy information such as presented herein enables a caregiver or clinician to see the complexity and amount of chaos for a particular case. In some embodiments, entropy information may be presented to a user, such as a clinician or caregiver, via interface 142 of FIG. 1A. In some embodiments, this information may be used for managing resources or raking action such as prescribing other treatments, based on the entropy. In particular, the disruption or chaos measured by entropy provides a valuable indicator for program management, health services, and provisioning. It is important to the accountable-care organizations to be able to figure out what is causing particular disruptions (or chaos) and then to design program changes to mitigate that, since the degree of chaos may be indicative of wasting their precious resources.

As shown in FIG. 5C, defenders ("def", top left-hand side) and midfielders ("mid", bottom right-hand side) exhibit a comparatively constant entropy ('disorder', randomness) in their patterns of injury through the year. Beginning with training in the winter, their injury sequences have trajectory entropy values that rise to about H=0.3 and stay relatively the same until exposure to injury risk drops at the end of the season. Forwards ("fwd", top right-hand side) have less variability in their acute injury sequences early in the year, a rounded 'crown' with entropy peaking at about H=0.4 in mid-season, followed by a reduced variability near the season's close. Not surprisingly, goal keepers ("gk", bottom left-hand side) have a less-disordered, homogeneous pattern of injuries early in the season, with an upward slope of increasing entropy as the season wears on. Initial injuries and early subsequent injuries give rise to progressively more diverse injury types in goal keepers until, near the end of the season, distinctive goal-keeping patterns predominate again.

At a step 250, in some embodiments, K-nearest neighbor distance calculations or another appropriate distance measures are determined. This optional step facilitates identifying the boundaries of the clusters. In some embodiments, this step includes taking the date-time coordinates associated with a candidate record to be matched and computing for each retrieved record the cluster distance that separates the candidate record from the centroid coordinates of the nearest trajectory cluster. In some embodiments, this step is performed using software services 126 of FIG. 1A, such as the open-source arulesSequences package.

In embodiments this step can be viewed as looking for proximity to the clusters produced in step 240 based on multiple variables. A centroid is associated with the clusters (such as those illustratively depicted in FIG. 3A-3C), in the multi-dimensional vector space, about which the distance of a particular member of that cluster may be characterized. In some embodiments, for each of the "rows" or timeseries, such as shown in FIGS. 6A and 6B, the arulesSequences software package returns an array with a cluster identification.

At a step 260, in some embodiments, candidate matches are sorted and ranked by cluster distances. This optional step facilitates the comparison of step 270 by reducing the number of comparisons, because, for a rank-ordered set of candidate matches, comparisons may be performed in order until candidate matches satisfy or fail the threshold comparison.

At a step 270, determine for the entity whether the distance d exceeds a threshold. In some embodiments, the threshold is an heuristic threshold. In some embodiments, the use case associated with the potential match is used to determine the threshold. For example, in a certain uses such as for broad populations, a lower threshold may be appropriate, but for an individual patient or athlete, a higher threshold may be used. In some embodiments, a care provider or clinician may set the threshold; the threshold may be set from a table of associated use-cases; or the threshold may be set based on the determined distances, for example, where there is a gap between successive rank-ordered cluster distances. In some embodiments, an agent of a multi-agent computer system, such as computer system 120 of FIG. 1A, is used to determine the threshold.

At a step 280, where the distance does not satisfy the threshold, then the entity is rejected as an improbable match that should not be linked with the candidate record. On the other hand, if for a given entity the distance is less than the threshold, then at a step 290, that particular cluster is indicated as a probable match for the candidate record. (In an embodiment, the entity associated with the candidate record is determined as being a member the particular cluster.) In some embodiments, these matches are reported to a clinician or caregiver, and may be reported as results displayed on interface 142 of FIG. 1A. In embodiments, the probable matches determined in step 280 merit consideration for preventive intervention that is well-suited to mitigating the serial-injury trajectory risks that are associated with members of that cluster.

With reference now to FIGS. 3A-3C, 4A-4C, and 5A-5C, output and results are shown for an example embodiment of the invention as applied to professional soccer. In this example records were randomly selected from a professional soccer athlete health records data warehouse, which was derived from Cerner Healthe Athlete™ electronic health record (EHR) from 100% of episodes of care that are incident upon the 22 teams that comprise a U.S. professional soccer league. Personally-identifiable information was removed in conformance with U.S. HIPAA law and regulations, and the de-identified data were stored in a separate, secure database. From a total of 5,110 injury-related encounters between 1 Jan. 2010 and 21 Nov. 2012 were identified a subset of 546 players who had 2 or more lower-extremity injury episodes during a calendar year in this 3-year, 3-season period. The large number of acute injuries and reinjuries to the lower extremities make these particularly well-suited to such quantitative analysis. In this example, and not as a limitation, the analysis was confined to acute (not chronic; not over-use) and to anatomical structures in the lower extremity (not other body parts).

Each injury is date-stamped according to the time of injury and time of resolution of the injury and return-to-play. The soccer-league data was recast in the form of sequences with week-level granularity, such as shown in the chart of FIG. 6B, and the sequences were analyzed using the R statistical trajectory-mining packages TraMineR and arulesSequences of software services 126, described in connection to FIG. 1A.

Application of embodiments of the invention in this instance were able to correctly and automatically establish clusters and cluster-membership and cluster-distance values for example candidate records and was able also to automatically detect characteristic differences in injuries that are associated with mechanical stresses and injury exposures by position played. Moreover, the system and method embodiments automatically discovered statistically significant 'trajectories' (patterns or sequences of consecutive injuries) that can be actionable and amenable to training or rehabilitation interventions specially designed to interdict or prevent the significant trajectories or patterns.

Figure 3A:
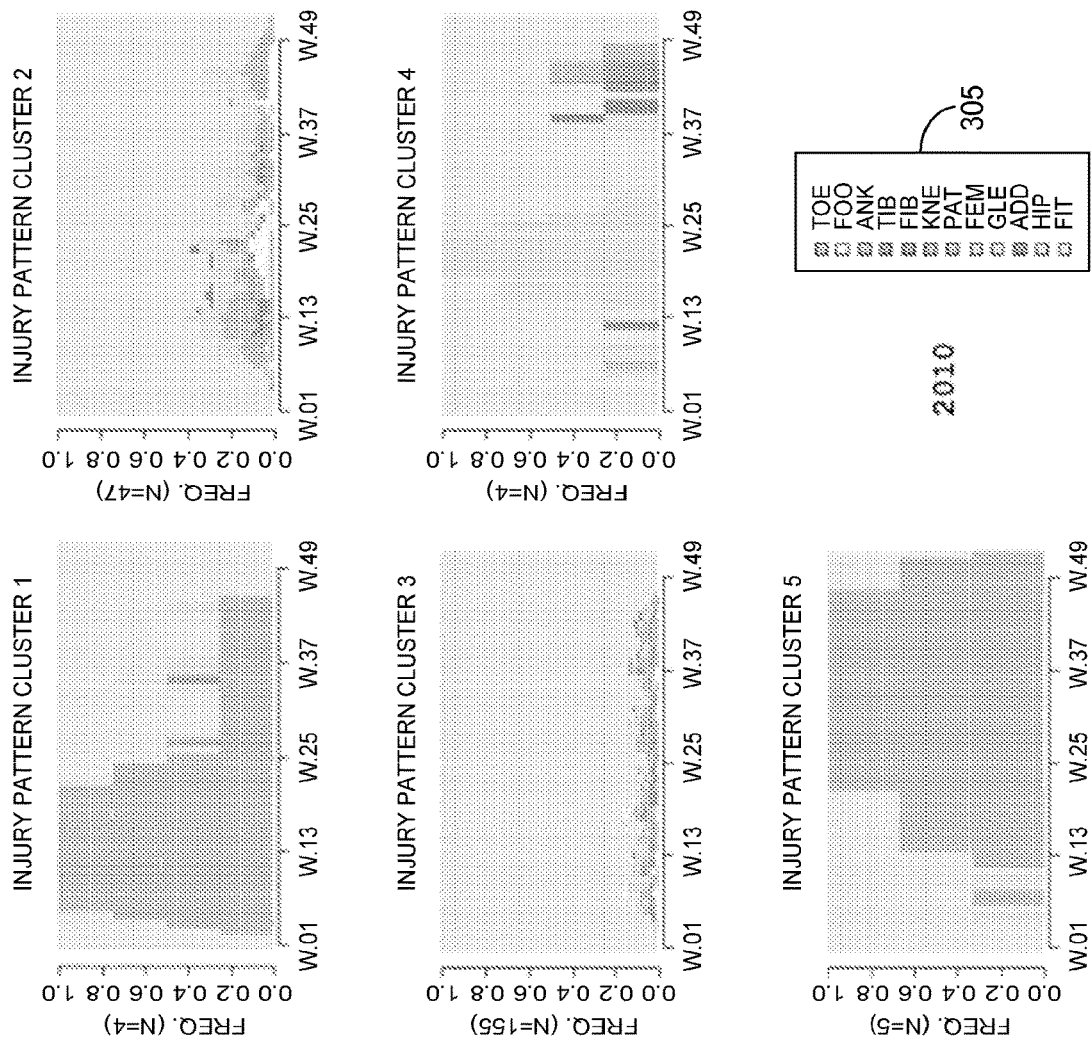
FIGS. 3A-3C depict pattern clusters of example serial lower-extremity injuries.
Figure 3B:
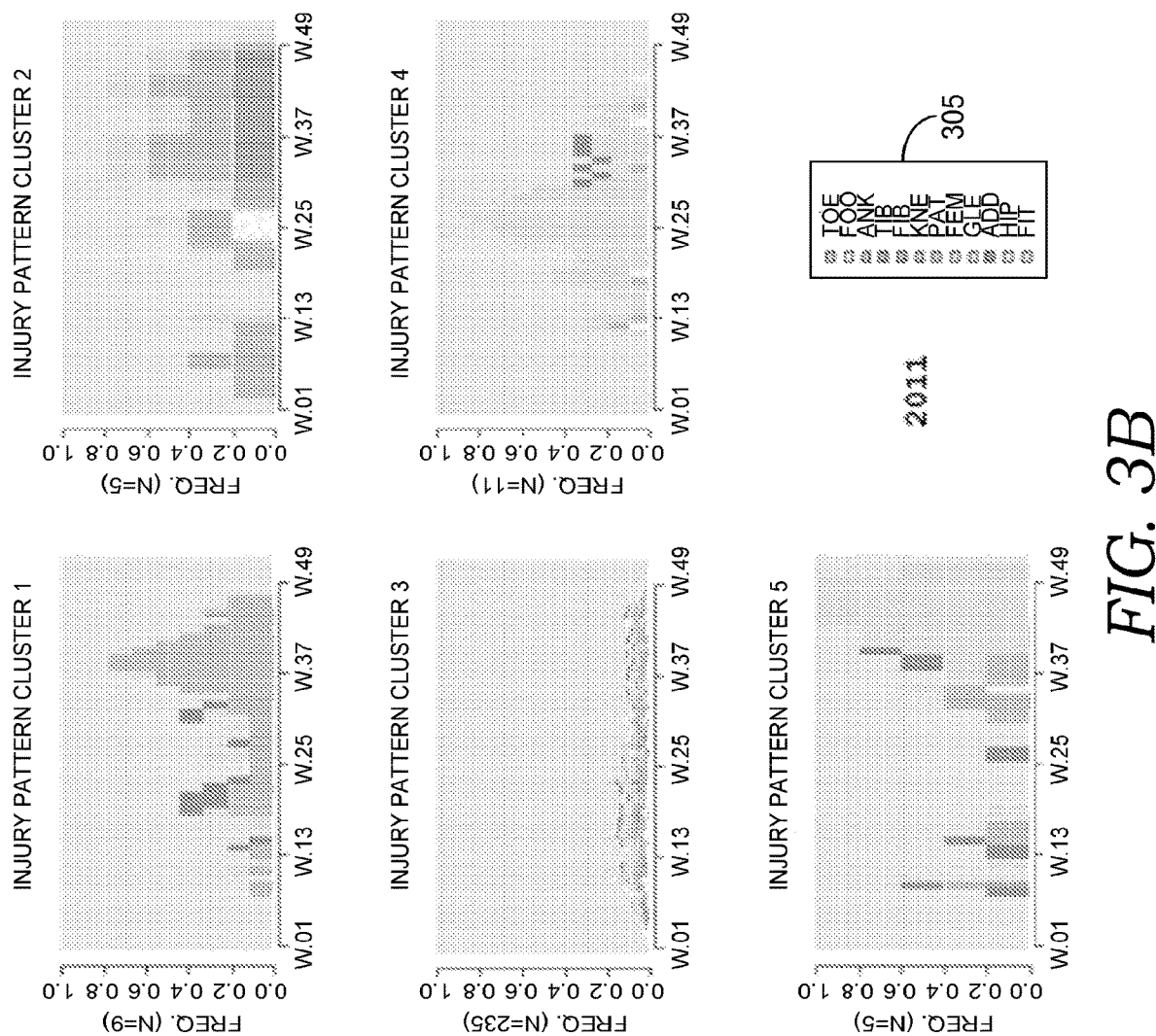
Figure 3C:
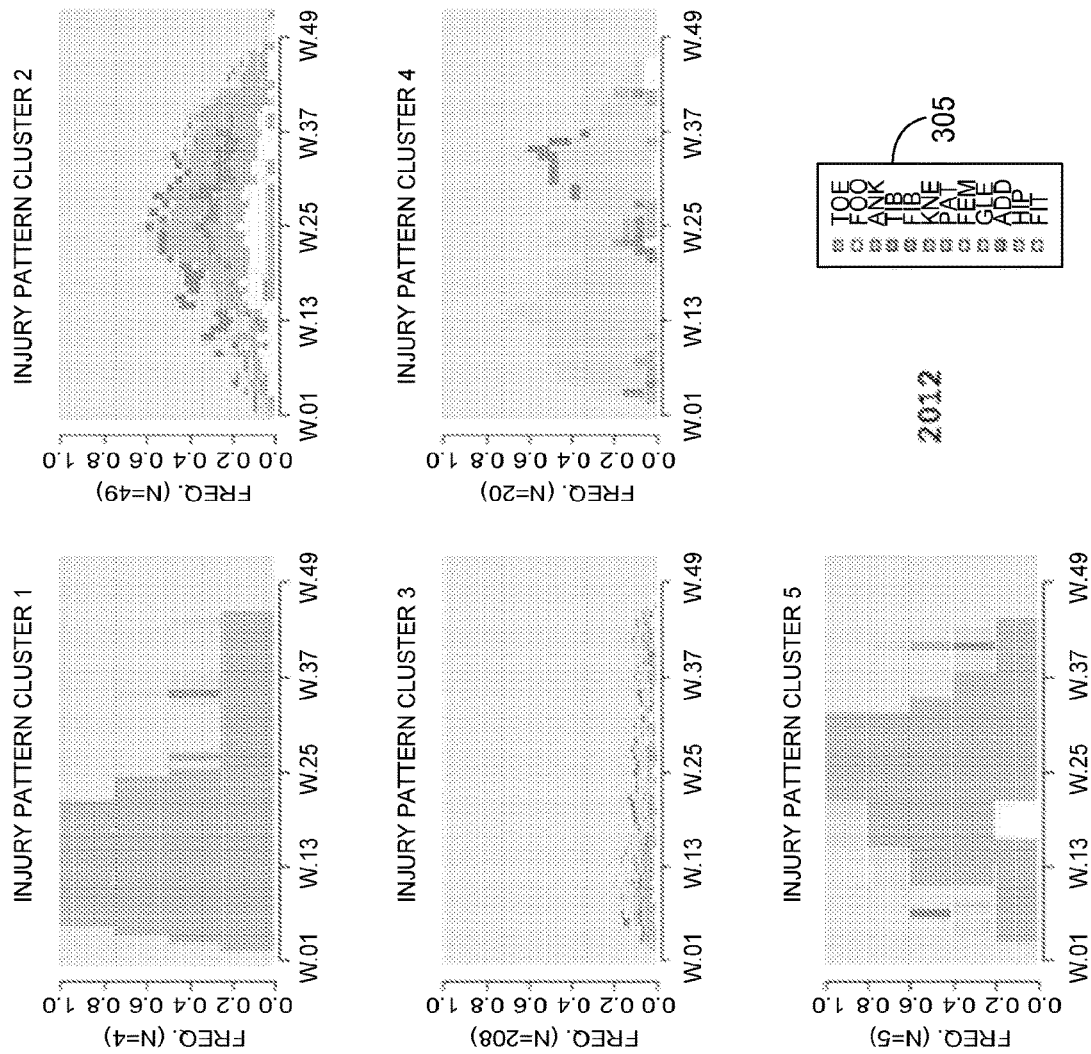

Turning now to FIGS. 3A, 3B, and 3C, illustrative examples of pattern clusters, such as generated by step 240 of method 200, based on the soccer-league data, are provided. In particular, each of FIGS. 3A, 3B, and 3C include data from 2010, 2011, and 2012, respectively, showing clusters of serial acute lower-extremity multi-injury trajectories. In each of 3A, 3B, and 3C, there are 5 main clusters or prevalent trajectory types, labeled Injury Pattern Cluster 1 ("cluster #1") through Injury Pattern Cluster 5 ("cluster #5"). A legend 305 indicates which injuries correspond to the colors of clusters 1 through 5, for each of 3A, 3B, and 3C.

For each of 3A, 3B, and 3C, cluster #3 consists of a 73% majority of players who manage to stay in fit playing condition for more than 80% of the 52 weeks in the year. It is unlikely that substantial improvements could be made here. We might consider this a "baseline" repeat-injury pattern, and in an embodiment, use this information for determining the threshold described in connection to step 270 of method 200. Cluster #4 consists of 7% of players in whom femoral injuries predominate. Thus, it is possible here that meaningful changes in prevention or training or equipment or other factors could yield significant reduction in this group. Cluster #5 represents the 2% of players who sustain moderate to severe knee injuries, especially in mid-season.

Cluster #1 involves 2% of players with acute ankle injuries of all severity levels, particularly arising early in the season, but the injuries are repeated and of such cumulative duration as to constitute a major impact to the team roster. This is logically consistent with research studies indicating that more than half of ankle injuries occurred in players who had one or more previous ankle sprain. Cluster #2 is a 16% subgroup of players whose injury trajectories are diverse with large variability and 4 to 5 times higher injury rate compared to cluster #3. It is likely that detailed analysis of this group may reveal style-of-play or behavioral differences that would be amenable to education and preventive steps to reduce risk in players who exhibit this pattern.

Figure 4A:
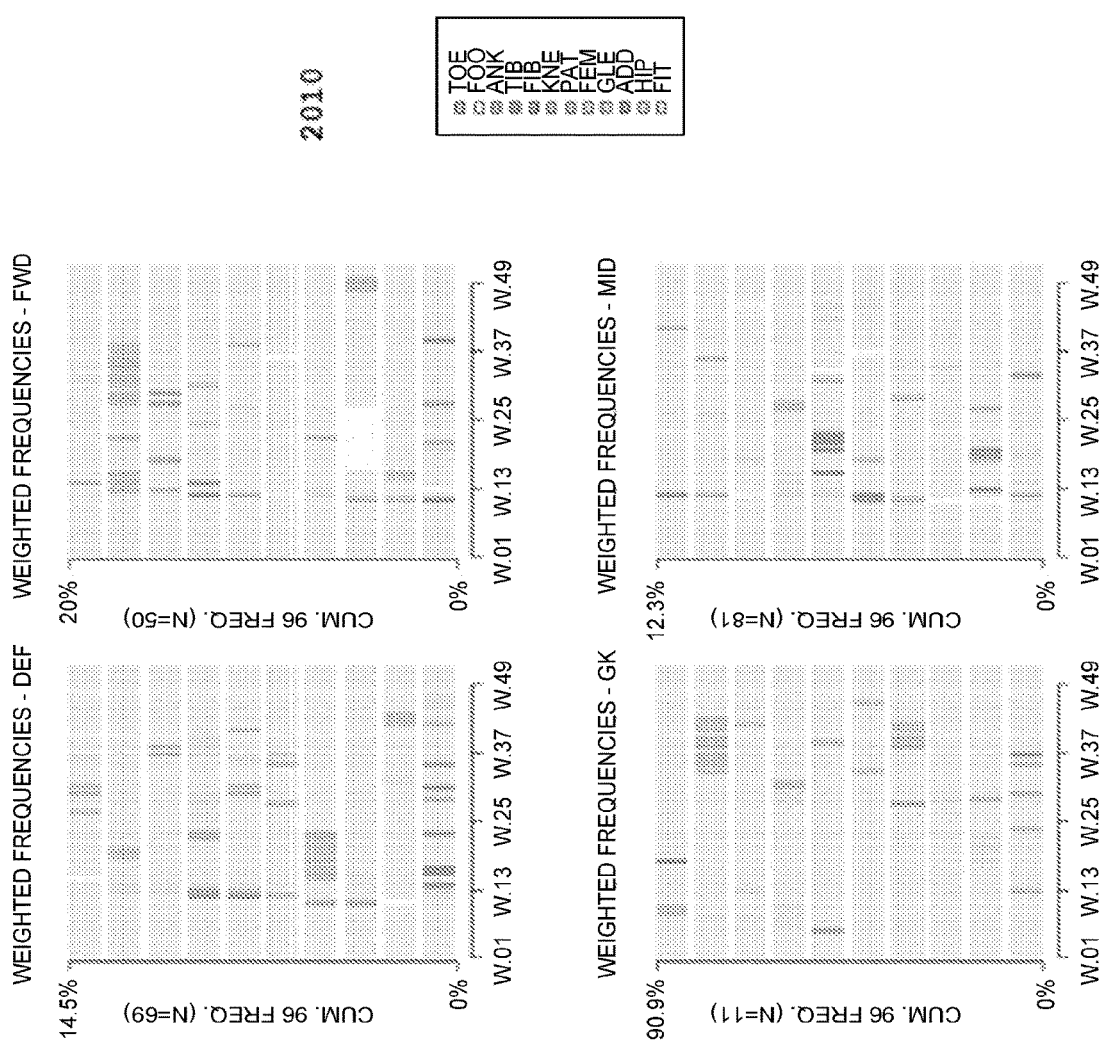
FIGS. 4A-4C depict pattern frequency by position of serial lower-extremity injuries.
Figure 4B:
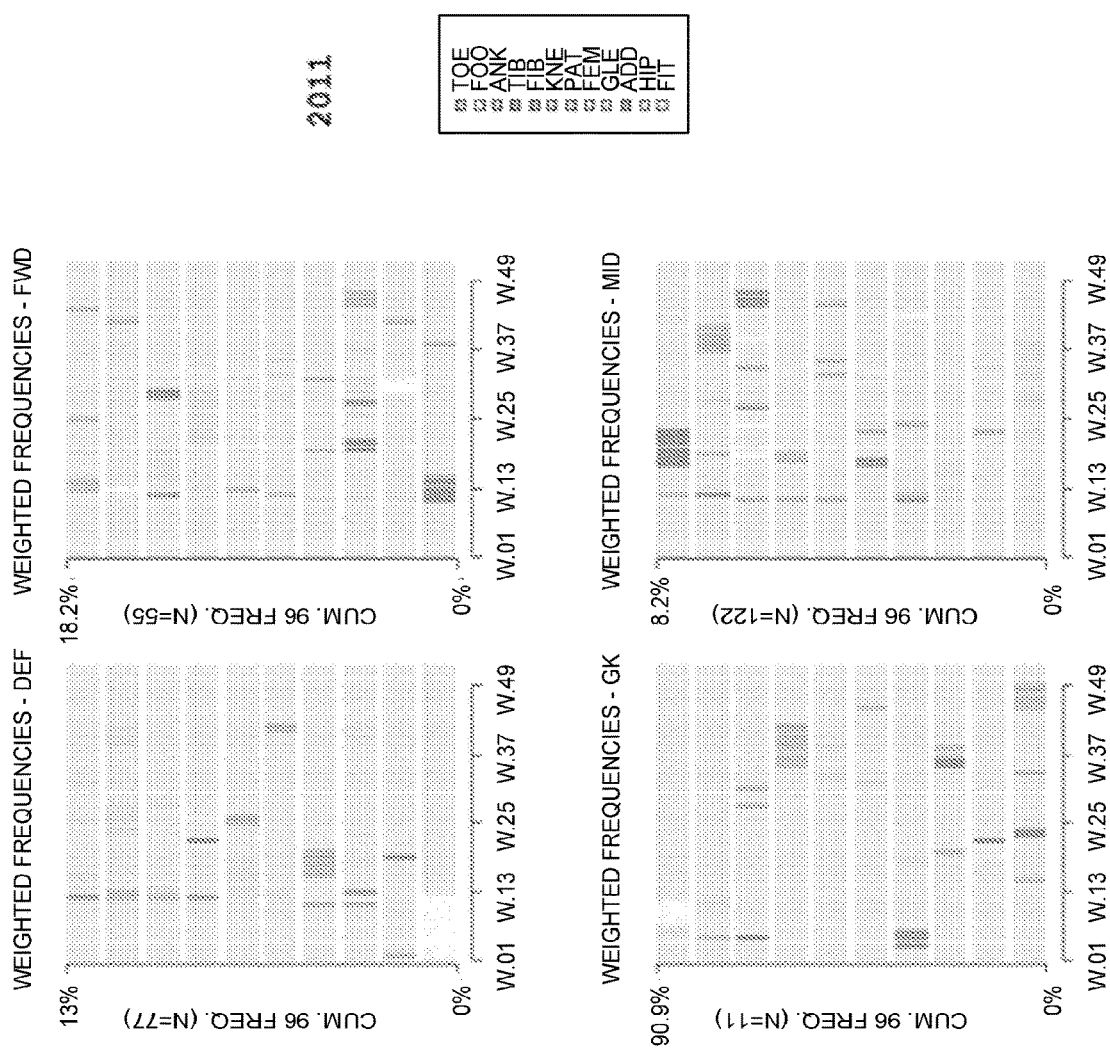
Figure 4C:
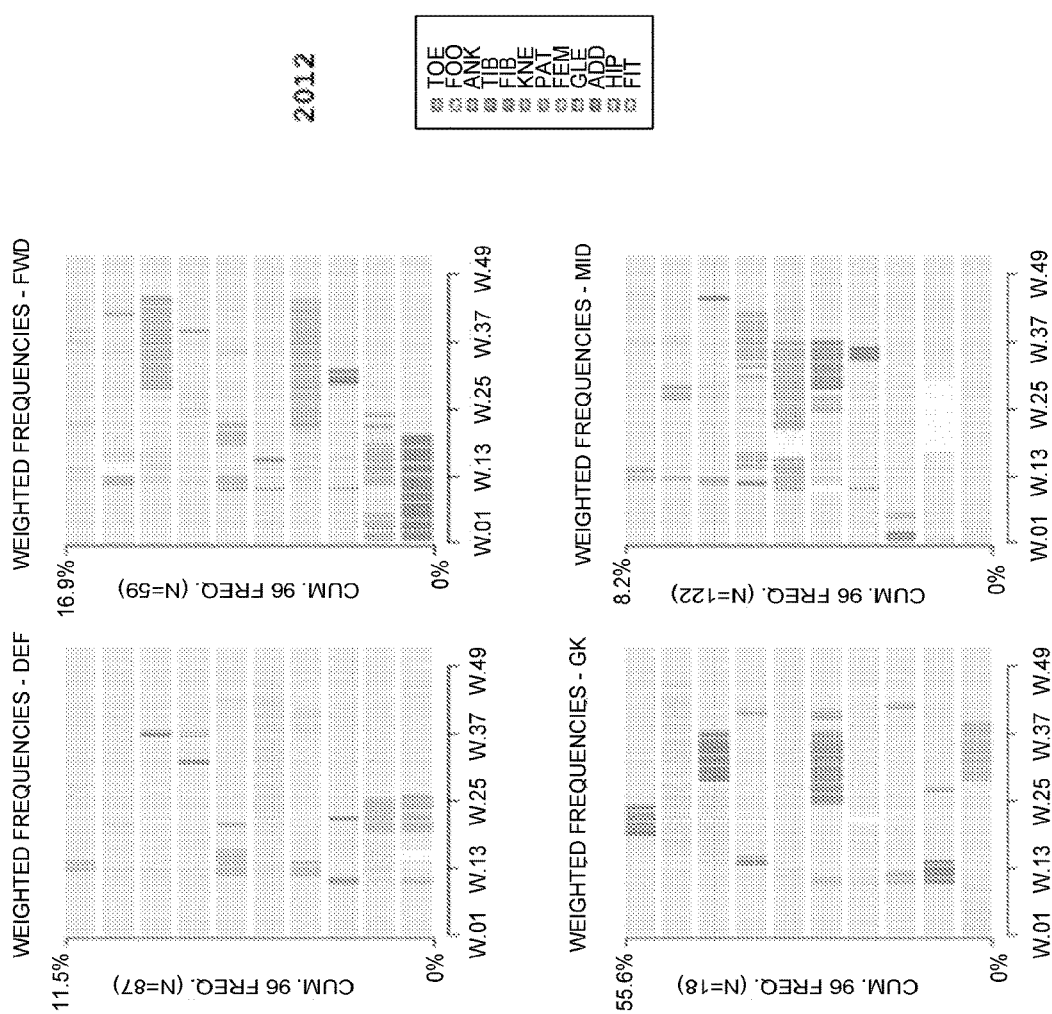

In all instances, the matching of a player's injury-trajectory against the patterns represented by these clusters, such as provided by embodiments of the invention, can reliably guide the prescribing of a specific intervention to mitigate the risks that are associated with the cluster to which a player belongs. FIGS. 4A-4C illustratively depict pattern frequency by position of serial lower-extremity injuries, based on the clusters of FIGS. 3A-3C.

Figure 8:
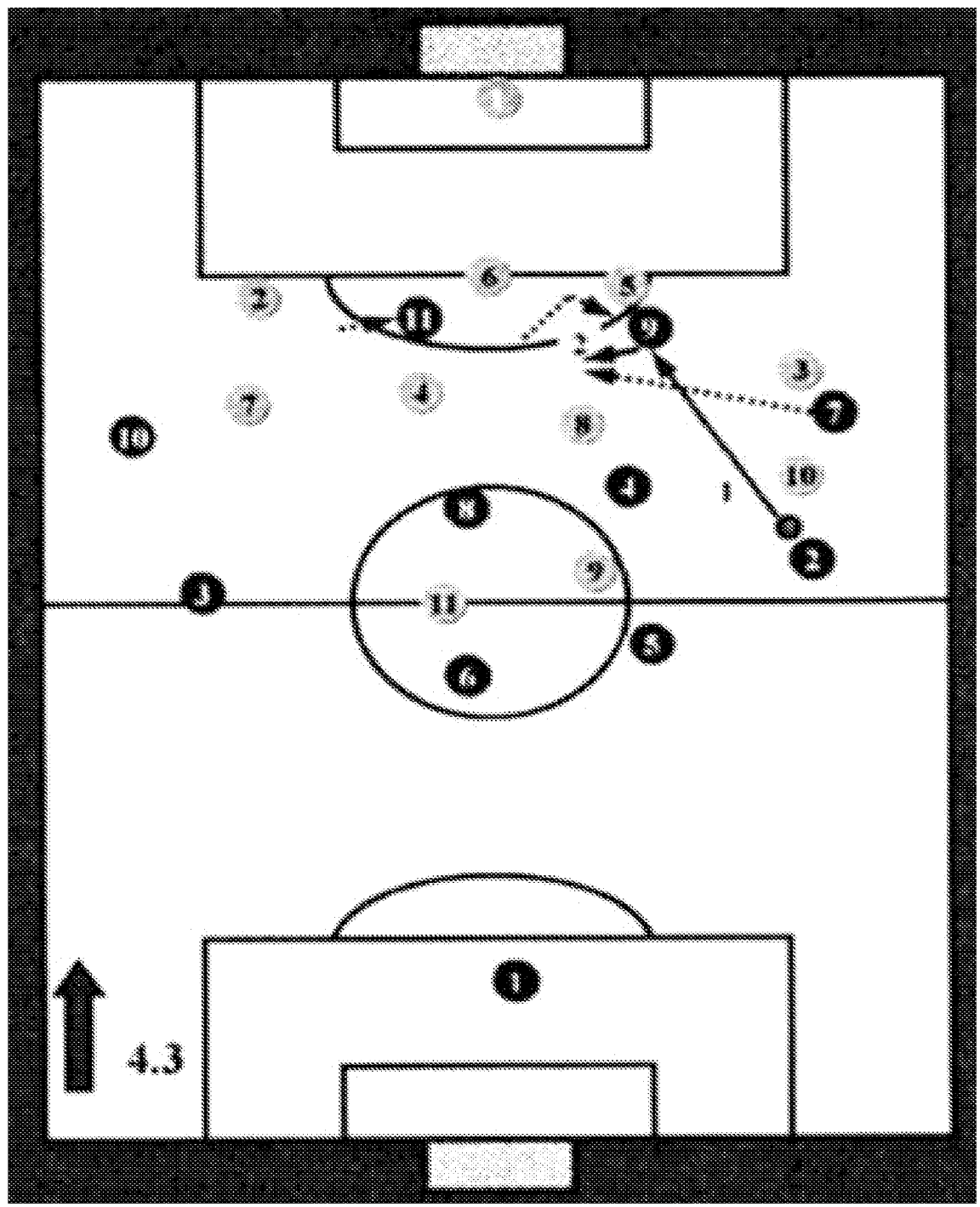
FIG. 8 provides an illustrative depiction of a soccer player play sequence for evaluating a pattern of play using embodiments of the invention.

Turning now to FIG. 8 there is provided an illustrative depiction of a soccer player play-sequence for evaluating a pattern of play using an embodiment of the invention. With reference to FIG. 8, some embodiments of the invention provide decision support for athletes, athletic and fitness managers and health care providers including for example, decision support regarding effectiveness of equipment, such as protective gear (e.g., shin guards, footwear, eyewear) or playing on artificial turf, and evaluation of equipment changes affecting injury reduction, injury-specific strength training, injury-specific ROM/flexibility training, balance/proprioception training (such as may be performed with BOSU, swiss ball, foam board.); in-game monitoring, play-pattern evaluation, and substitution decision making; effectiveness of safety-oriented rules; impact of other rules on injury, for example.

In the example play sequence shown in FIG. 8, initially player 2 has possession of the ball. Player 7, a mid fielder, cuts between player 9, a forward, and the ball is transferred to player 9. At this point there are three players on the offense vs. two players on defense (in the area that matters).

This outnumbering likely creates an increased risk of injury for the two defensive players and a diminished risk of injury for the three offensive players. An embodiment of the invention can be used to determine the effect of this pairing in terms of the risk on offense and defense. Moreover, evaluating this risk is not only useful to the health of the player, but also to the owner and management. For example, in terms of pre-match strategy, a clearer understanding of the risk, as provided by embodiments of the invention, may lead the management to accept the risk in turn for increasing likelihood of defeating the opposing team.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more non-transitory computer-readable storage devices having computer-usable instructions embodied thereon that, when executed, enable a given processor to perform a method for determining return-to-play time for an injured athlete, the method comprising:
    receiving a first set of health records of an electronic health-records system in communication with a clinician interface, associated with a reference population of athletes, including injury information for each athlete in the reference population of athletes, the first set of health records being stored on at least one data store;
    receiving attribute information specifying one or more athletic or clinical attributes of interest for the reference population of athletes;
    determining a set of athlete injury timeseries longitudinal patterns for each athlete in the population, each athlete injury timeseries longitudinal pattern of the set comprising injury information and inter-episode time interval information between injury episodes corresponding to each athlete of the reference population of athletes;
    based on the set of athlete injury timeseries longitudinal patterns for the reference population of athletes, determining a set of injury trajectory clusters by performing a single database scan that uses a vertical identification-list database format, wherein the database scan occurs on one or more data stores of electronic health records distributed across multiple physical locations, applying a multi-cluster determinate to each timeseries longitudinal pattern, and extracting one or more cluster assignments, wherein each athlete injury trajectory cluster has a centroid;
    receiving a second set of health records, the second set of health records associated with the injured athlete, the second set of health records including injury information for the injured athlete;
    determining a timeseries longitudinal pattern from the second set of health records comprising injury information and inter-episode time intervals between injury episodes of the injured athlete, thereby forming an injured athlete timeseries longitudinal pattern;
    for each cluster in the set of injury trajectory clusters, determining a cluster distance between the injured athlete timeseries longitudinal pattern and the centroid of the cluster, thereby forming a set of cluster distances corresponding to the set of clusters;
    from the set of cluster distances, matching the injured athlete to the cluster corresponding to a smallest cluster distance;
    automatically determining, by the processor, a recommendation for treatment based on the matching of the injured athlete to the cluster; and
    presenting the recommendation via the clinician interface.

2. The one or more computer-readable storage devices of claim 1 further comprising based on the matched cluster, determining a return-to-play time for the injured athlete.

3. The computer readable storage devices of claim 1, further comprising: determining a cluster distance threshold for each injury trajectory cluster and assigning the distance threshold to each injury trajectory cluster.

4. The computer readable storage devices of claim 1, further comprising: automatically generating a management plan for the injured athlete.

5. The computer readable storage devices of claim 3, further comprising: providing an electronic notification to a caregiver of the injured athlete based on a determination that the injured athlete exhibits a pattern of injury events similar to a portion of the reference population of athletes.

6. The computer-readable storage devices of claim 5, wherein the determining is done by matching timeseries from the second set of health records to at least one injury temporal pattern associated with the portion of the reference population of athletes and calculated based in part on the inter-episode time interval information.

7. The computer-readable storage devices of claim 5, further comprising:
    for each cluster of the set of injury trajectory clusters:
        (1) calculating the cluster distance between the exhibited pattern of injury events and the centroid of the cluster;
        (2) performing a comparison of the cluster distance and the cluster distance threshold;
        (3) based on the comparison, determining that the threshold is satisfied; and
        (4) associating the injured athlete exhibiting the pattern of injury events with the portion of the reference population of athletes corresponding to the injury trajectory cluster.

8. The computer-readable storage devices of claim 7, wherein the cluster distance threshold is determined based on attribute information associated with the reference population; and wherein the cluster distance threshold is satisfied if the cluster distance is less than or equal to the threshold.

9. The computer-readable storage devices of claim 3, wherein the cluster distance threshold is determined based on the received attribute information.

10. The computer-readable storage devices of claim 1, further comprising, for at least one cluster associated with the injured athlete, at least one of: providing an indication of the association to a caregiver associated with the injured athlete, determining an injury risk reduction regimen, determining a likelihood of risk of re-injury, and determining a return-to-play time value.

11. One or more non-transitory computer-readable media having computer-usable instructions embodied thereon that, when executed by a computer processor, enable the computer processor to perform a method for discovering context-specific serial injury trajectories, the method comprising:
- receiving a first set of health records of an electronic health-records system in communication with a clinician interface, associated with a reference population of athletes, including injury information for each athlete in the reference population of athletes, the first set of health records being stored on at least one data store;
- receiving attribute information specifying one or more athletic or clinical attributes of interest for the reference population of athletes;
- determining a set of athlete injury timeseries longitudinal patterns for each athlete in the population, each athlete injury timeseries longitudinal pattern of the set comprising injury information and inter-episode time interval information between injury episodes corresponding to each athlete of the reference population of athletes;
- based on the set of athlete injury timeseries longitudinal patterns for the reference population of athletes, determining a set of injury trajectory clusters by performing a single database scan that uses a vertical identification-list database format, wherein the database scan occurs on one or more data stores of electronic health records distributed across multiple physical locations, applying a multi-cluster determinate to each timeseries longitudinal pattern and extracting one or more cluster assignments, wherein each athlete injury trajectory cluster has a centroid;
- receiving a second set of health records, the second set of health records associated with an injured athlete, the second set of health records including injury information for the injured athlete;
- determining a timeseries longitudinal pattern from the second set of health records comprising injury information and inter-episode time intervals between injury episodes of the injured athlete, thereby forming an injured athlete timeseries longitudinal pattern; for each cluster in the set of injury trajectory clusters, determining a cluster distance between the injured athlete timeseries longitudinal pattern and the centroid of the cluster, thereby forming a set of cluster distances corresponding to the set of clusters;
- from the set of cluster distances, matching the injured athlete to the cluster corresponding to a smallest cluster distance;
- automatically determining, by the computer processor, a recommendation for treatment based on the matching of the injured athlete to the cluster; and
- presenting the recommendation via the clinician interface.

12. The computer-readable-media of claim 11, further comprising: determining a cluster distance threshold for each injury trajectory cluster and assigning the distance threshold to each injury trajectory cluster.

13. The computer-readable media of claim 11, further comprising: automatically generating a management plan for the injured athlete.

14. The computer-readable media of claim 13, further comprising: providing an electronic notification to a caregiver of the injured athlete based on a determination that the injured athlete exhibits a pattern of injury events similar to a portion of the reference population of athletes.

15. The computer-readable media of claim 14, wherein the determining is done by matching timeseries from the second set of health records to at least one injury temporal pattern associated with the portion of the reference population of athletes and calculated based in part on the inter-episode time interval information.

16. The computer-readable media of claim 15, further comprising:
- for each cluster of the set of injury trajectory clusters:
  - (1) calculating a cluster distance between the exhibited pattern of injury events and the centroid of the cluster;
  - (2) performing a comparison of the cluster distance and the cluster distance threshold;
  - (3) based on the comparison, determining that the threshold is satisfied; and
  - (4) associating the injured athlete exhibiting the pattern of injury events with the portion of the reference population of athletes corresponding to the injury trajectory cluster.

17. A computer-implemented method to facilitate reducing risk of injury in a population of athletes, the method comprising:
- receiving a first set of health records of an electronic health-records system in communication with a clinician interface, associated with a reference population of athletes, including injury information for each athlete in the reference population of athletes, the first set of health records being stored on at least one data store;
- receiving attribute information specifying one or more athletic or clinical attributes of interest for the reference population of athletes;
- determining a set of athlete injury timeseries longitudinal patterns for each athlete in the population, each athlete injury timeseries longitudinal pattern of the set comprising injury information and inter-episode time interval information between injury episodes corresponding to each athlete of the reference population of athletes;
- based on the set of athlete injury timeseries longitudinal patterns for the reference population of athletes, determining a set of injury trajectory clusters by performing a single database scan that uses a vertical identification-list database format, wherein the database scan occurs on one or more data stores of electronic health records distributed across multiple physical locations, applying a multi-cluster determinate to each timeseries longitudinal pattern and extracting one or more cluster assignments, wherein each athlete injury trajectory cluster has a centroid;
- receiving a second set of health records, the second set of health records associated with an injured athlete, the second set of health records including injury information for the injured athlete;
- determining a timeseries longitudinal pattern from the second set of health records comprising injury information and inter-episode time intervals between injury episodes of the injured athlete, thereby forming an injured athlete timeseries longitudinal pattern;
- for each cluster in the set of injury trajectory clusters, determining a cluster distance between the injured athlete timeseries longitudinal pattern and the centroid of the cluster, thereby forming a set of cluster distances corresponding to the set of clusters;
- from the set of cluster distances, matching the injured athlete to the cluster corresponding to a smallest cluster distance;

automatically determining, by a computer processor, a recommendation for treatment based on the matching of the injured athlete to the cluster; and presenting the recommendation via the clinician interface.

18. The method of claim 17, wherein the cluster distance threshold is determined based on attribute information associated with the reference population; and wherein the cluster distance threshold is satisfied if the cluster distance is less than or equal to the threshold.

19. The method of claim 17, wherein the cluster distance threshold is determined based on the received attribute information.

20. The method of claim 17, further comprising, for at least one cluster associated with the injured athlete, at least one of: providing an indication of the association to a caregiver associated with the injured athlete, determining an injury risk reduction regimen, determining a likelihood of risk of re-injury, and determining a return-to-play time value.

* * * * *